United States Patent
Pudil et al.

(10) Patent No.: US 10,343,145 B2
(45) Date of Patent: Jul. 9, 2019

(54) ZIRCONIUM PHOSPHATE RECHARGING METHOD AND APPARATUS

(71) Applicant: Medtronic, Inc., Minneapolis, MN (US)

(72) Inventors: Bryant J. Pudil, Plymouth, MN (US); Martin T. Gerber, Maple Grove, MN (US); Christopher M. Hobot, Tonka Bay, MN (US)

(73) Assignee: Medtronic, Inc., Minneapolis, MN (US)

(*) Notice: Subject to any disclaimer, the term of this patent is extended or adjusted under 35 U.S.C. 154(b) by 0 days.

(21) Appl. No.: 16/047,245

(22) Filed: Jul. 27, 2018

(65) Prior Publication Data

US 2019/0001303 A1    Jan. 3, 2019

Related U.S. Application Data

(60) Division of application No. 14/722,119, filed on May 26, 2015, now Pat. No. 10,052,612, which is a (Continued)

(51) Int. Cl.
*B01J 20/34* (2006.01)
*A61M 1/16* (2006.01)
(Continued)

(52) U.S. Cl.
CPC ........ *B01J 20/3475* (2013.01); *A61M 1/1696* (2013.01); *B01J 20/0211* (2013.01); *B01J 20/3483* (2013.01); *B01J 39/09* (2017.01)

(58) Field of Classification Search
None
See application file for complete search history.

(56) References Cited

U.S. PATENT DOCUMENTS

| 1,617,288 A | 2/1927 | Kenney |
| 2,703,313 A | 1/1950 | Gill |

(Continued)

FOREIGN PATENT DOCUMENTS

| CN | 1487853 A | 4/2004 |
| CN | 102573618 | 7/2012 |

(Continued)

OTHER PUBLICATIONS

[NPL244] U.S. Appl. No. 13/836,079, filed Mar. 15, 2013.

(Continued)

*Primary Examiner* — Richard C Gurtowski
(74) *Attorney, Agent, or Firm* — Kenneth Collier; Roger Hahn

(57) ABSTRACT

Methods and related apparatuses for sorbent recharging are provided. The methods and related apparatuses for recharging can recharge a specific rechargeable layer or module of a sorbent material such as zirconium phosphate in a sorbent cartridge. The methods and apparatuses include a fluid source containing at least one recharging fluid, wherein the fluid source is fluidly connectable to at least one rechargeable sorbent module for use in sorbent dialysis in a fluid flow path. The methods and apparatuses include passing a single solution through the zirconium phosphate for ion exchanges, resulting in zirconium phosphate to maintain a substantially consistent pH in a dialysate used during dialysis.

20 Claims, 10 Drawing Sheets

Related U.S. Application Data continuation-in-part of application No. 14/642,847, filed on Mar. 10, 2015, now Pat. No. 9,974,896, which is a continuation-in-part of application No. 14/261,651, filed on Apr. 25, 2014, now Pat. No. 9,895,477.

(60) Provisional application No. 62/077,159, filed on Nov. 7, 2014, provisional application No. 62/016,613, filed on Jun. 24, 2014, provisional application No. 61/909,372, filed on Nov. 26, 2013, provisional application No. 61/941,672, filed on Feb. 19, 2014.

(51) Int. Cl.
*B01J 20/02* (2006.01)
*B01J 39/09* (2017.01)

(56) References Cited

U.S. PATENT DOCUMENTS

| | | | |
|---|---|---|---|
| 3,608,729 A | 9/1971 | Haselden |
| 3,617,558 A | 11/1971 | Jones |
| 3,669,880 A | 6/1972 | Marantz |
| 3,776,819 A | 12/1973 | Williams |
| 3,840,835 A | 10/1974 | Kussy |
| 3,850,835 A | 11/1974 | Marantz |
| 3,884,808 A | 5/1975 | Scott |
| 3,902,490 A | 9/1975 | Jacobsen |
| 3,989,622 A | 11/1976 | Marantz |
| 4,073,725 A | 2/1978 | Takeuchi |
| 4,094,775 A | 6/1978 | Mueller |
| 4,192,748 A | 3/1980 | Hyden |
| 4,206,054 A | 6/1980 | Moore |
| 4,209,392 A | 6/1980 | Wallace |
| 4,376,707 A | 3/1983 | Lehmann |
| 4,460,555 A | 7/1984 | Thompson |
| 4,581,141 A | 4/1986 | Ash |
| 4,650,587 A | 3/1987 | Polak |
| 4,661,246 A | 4/1987 | Ash |
| 4,684,460 A | 8/1987 | Issautier |
| 4,687,582 A | 8/1987 | Dixon |
| 5,230,702 A | 7/1993 | Lindsay |
| 5,284,470 A | 2/1994 | Beltz |
| 5,302,288 A | 4/1994 | Meidl |
| 5,308,315 A | 5/1994 | Khuri |
| 5,507,723 A | 4/1996 | Keshaviah |
| 5,662,806 A | 9/1997 | Keshaviah et al. |
| 5,770,086 A | 6/1998 | Indriksons |
| 5,849,179 A | 12/1998 | Emerson |
| 5,858,186 A | 1/1999 | Glass |
| 5,944,684 A | 8/1999 | Roberts |
| 6,036,858 A | 3/2000 | Carlsson |
| 6,114,176 A | 9/2000 | Edgson et al. |
| 6,126,831 A | 10/2000 | Goldau |
| 6,521,184 B1 | 2/2003 | Edgson et al. |
| 6,572,769 B2 | 6/2003 | Rajan |
| 6,579,460 B1 | 6/2003 | Willis |
| 6,627,164 B1 | 9/2003 | Wong |
| 6,666,840 B1 | 12/2003 | Falkvall et al. |
| 6,719,745 B1 | 4/2004 | Taylor |
| 6,814,724 B2 | 11/2004 | Taylor |
| 6,818,196 B2 | 11/2004 | Wong |
| 6,861,266 B1 | 3/2005 | Sternby |
| 6,878,258 B2 | 4/2005 | Hughes |
| 6,878,283 B2 | 4/2005 | Thompson |
| 6,878,285 B2 | 4/2005 | Hughes |
| 6,960,179 B2 | 11/2005 | Gura |
| 7,033,498 B2 | 4/2006 | Wong |
| 7,101,519 B2 | 9/2006 | Wong |
| 7,208,092 B2 | 4/2007 | Micheli |
| 7,241,272 B2 | 7/2007 | Karoor |
| 7,276,042 B2 | 10/2007 | Polaschegg |
| 7,326,576 B2 | 2/2008 | Womble et al. |
| 7,435,342 B2 | 10/2008 | Tsukamoto |
| 7,488,447 B2 | 2/2009 | Sternby |
| 7,537,688 B2 | 5/2009 | Tarumi |
| 7,544,300 B2 | 6/2009 | Brugger |
| 7,544,737 B2 | 6/2009 | Poss |
| 7,563,240 B2 | 7/2009 | Gross |
| 7,566,432 B2 | 7/2009 | Wong |
| 7,597,806 B2 | 10/2009 | Uchi |
| 7,776,210 B2 | 8/2010 | Rosenbaum |
| 7,794,419 B2 | 9/2010 | Paolini |
| 7,850,635 B2 | 12/2010 | Polaschegg |
| 7,922,686 B2 | 4/2011 | Childers |
| 7,922,911 B2 | 4/2011 | Micheli |
| 7,947,179 B2 | 5/2011 | Rosenbaum |
| 7,955,290 B2 | 6/2011 | Karoor |
| 7,988,854 B2 | 8/2011 | Tsukamoto |
| 8,002,726 B2 | 8/2011 | Karoor |
| 8,012,118 B2 | 9/2011 | Curtin |
| 8,029,454 B2 | 10/2011 | Kelly |
| 8,066,658 B2 | 11/2011 | Karoor |
| 8,080,161 B2 | 12/2011 | Ding et al. |
| 8,087,303 B2 | 1/2012 | Beavis |
| 8,096,969 B2 | 1/2012 | Roberts |
| 8,180,574 B2 | 5/2012 | Lo |
| 8,187,250 B2 | 5/2012 | Roberts |
| 8,197,439 B2 | 6/2012 | Wang |
| 8,303,532 B2 | 11/2012 | Hamada |
| 8,404,491 B2 | 3/2013 | Li |
| 8,409,444 B2 | 4/2013 | Wong |
| 8,480,607 B2 | 7/2013 | Davies |
| 8,647,506 B2 | 2/2014 | Wong |
| 8,733,559 B2 | 5/2014 | Wong |
| 8,764,981 B2 | 7/2014 | Ding |
| 8,777,892 B2 | 7/2014 | Sandford |
| 9,144,640 B2 | 9/2015 | Pudil |
| 9,254,355 B2 | 2/2016 | Sandford |
| 9,527,015 B2 | 12/2016 | Chau |
| 2001/0007931 A1 | 7/2001 | Blatter |
| 2001/0009756 A1 | 7/2001 | Hei et al. |
| 2002/0016550 A1 | 2/2002 | Sweeney |
| 2002/0112609 A1 | 8/2002 | Wong |
| 2002/0117436 A1 | 8/2002 | Rajan |
| 2003/0080059 A1 | 5/2003 | Peterson et al. |
| 2003/0097086 A1 | 5/2003 | Gura |
| 2003/0105435 A1 | 6/2003 | Taylor |
| 2003/0113931 A1 | 6/2003 | Pan |
| 2003/0114787 A1 | 6/2003 | Gura |
| 2003/0187479 A1 | 10/2003 | Thong |
| 2004/0019312 A1 | 1/2004 | Childers |
| 2004/0099593 A1 | 5/2004 | DePaolis |
| 2004/0147900 A1 | 7/2004 | Polaschegg |
| 2004/0168963 A1 | 9/2004 | King |
| 2004/0257409 A1 | 12/2004 | Cheok |
| 2005/0006296 A1 | 1/2005 | Sullivan |
| 2005/0056592 A1 | 3/2005 | Braunger |
| 2005/0101901 A1 | 5/2005 | Gura |
| 2005/0113796 A1 | 5/2005 | Taylor |
| 2005/0150832 A1 | 7/2005 | Tsukamoto |
| 2005/0234354 A1 | 10/2005 | Rowlandson |
| 2005/0274658 A1 | 12/2005 | Rosenbaum |
| 2006/0037483 A1 | 2/2006 | Kief |
| 2006/0241543 A1 | 10/2006 | Gura |
| 2007/0007208 A1 | 1/2007 | Brugger et al. |
| 2007/0179431 A1 | 8/2007 | Roberts |
| 2007/0213665 A1 | 9/2007 | Curtin |
| 2008/0006570 A1 | 1/2008 | Gura |
| 2008/0011664 A1 | 1/2008 | Karoor |
| 2008/0051696 A1 | 2/2008 | Curtin |
| 2008/0053905 A9 | 3/2008 | Brugger et al. |
| 2008/0217245 A1 | 9/2008 | Rambod |
| 2008/0241031 A1 | 10/2008 | Li |
| 2008/0292935 A1* | 11/2008 | Roelofs .............. C08F 8/22 |
| | | 429/492 |
| 2009/0020471 A1 | 1/2009 | Tsukamoto |
| 2009/0078636 A1 | 3/2009 | Uchi |
| 2009/0101552 A1 | 4/2009 | Fulkerson |
| 2009/0120864 A1 | 5/2009 | Fulkerson |
| 2009/0216045 A1 | 8/2009 | Singh |
| 2009/0266358 A1 | 10/2009 | Sacristan Rock |
| 2009/0282980 A1 | 11/2009 | Gura |
| 2010/0004588 A1 | 1/2010 | Yeh |

(56) References Cited

U.S. PATENT DOCUMENTS

| | | |
|---|---|---|
| 2010/0007838 A1 | 1/2010 | Fujimoto |
| 2010/0078381 A1 | 4/2010 | Merchant |
| 2010/0078387 A1 | 4/2010 | Wong |
| 2010/0084330 A1 | 4/2010 | Wong |
| 2010/0100027 A1 | 4/2010 | Schilthuizen |
| 2010/0101195 A1 | 4/2010 | Clements |
| 2010/0102190 A1 | 4/2010 | Zhu et al. |
| 2010/0114012 A1 | 5/2010 | Sandford |
| 2010/0217181 A1 | 8/2010 | Roberts |
| 2010/0224492 A1 | 9/2010 | Ding et al. |
| 2010/0312172 A1 | 12/2010 | Hoffman |
| 2010/0312174 A1 | 12/2010 | Hoffman |
| 2010/0314314 A1 | 12/2010 | Ding |
| 2011/0009798 A1 | 1/2011 | Kelly |
| 2011/0017665 A1 | 1/2011 | Updyke |
| 2011/0048949 A1 | 3/2011 | Ding et al. |
| 2011/0079558 A1 | 4/2011 | Raimann |
| 2011/0163034 A1 | 7/2011 | Castellarnau |
| 2011/0171713 A1 | 7/2011 | Bluchel |
| 2011/0184340 A1 | 7/2011 | Tan |
| 2011/0272352 A1 | 11/2011 | Braig |
| 2011/0297593 A1 | 12/2011 | Kelly |
| 2012/0018377 A1 | 1/2012 | Tsukamoto |
| 2012/0095402 A1 | 4/2012 | Lande |
| 2012/0248017 A1 | 10/2012 | Beiriger |
| 2012/0273354 A1 | 11/2012 | Orhan et al. |
| 2012/0303079 A1 | 11/2012 | Mahajan |
| 2013/0018095 A1 | 1/2013 | Vath |
| 2013/0019179 A1 | 1/2013 | Zhao |
| 2013/0027214 A1 | 1/2013 | Eng |
| 2013/0028809 A1 | 1/2013 | Barton |
| 2013/0030356 A1 | 1/2013 | Ding |
| 2013/0116578 A1 | 5/2013 | An |
| 2013/0199998 A1 | 8/2013 | Kelly |
| 2013/0213890 A1 | 8/2013 | Kelly |
| 2013/0213891 A1 | 8/2013 | Karoor |
| 2014/0001112 A1 | 1/2014 | Karoor |
| 2014/0138294 A1 | 5/2014 | Fulkerson |
| 2014/0158588 A1 | 6/2014 | Pudil |
| 2014/0158623 A1 | 6/2014 | Pudil |
| 2014/0190885 A1 | 7/2014 | Meyer |
| 2014/0190891 A1 | 7/2014 | Lura |
| 2014/0217028 A1 | 8/2014 | Pudil |
| 2014/0251908 A1 | 9/2014 | Ding |
| 2014/0326671 A1 | 11/2014 | Kelly |
| 2014/0336568 A1 | 11/2014 | Wong |
| 2015/0057602 A1 | 2/2015 | Mason |
| 2015/0108069 A1 | 4/2015 | Merchant |
| 2015/0108609 A1 | 4/2015 | Kushida |
| 2015/0114891 A1 | 4/2015 | Meyer |
| 2015/0144539 A1 | 5/2015 | Pudil |
| 2015/0144542 A1 | 5/2015 | Pudil |
| 2015/0157960 A1 | 6/2015 | Pudil |
| 2015/0238673 A1 | 8/2015 | Gerber |
| 2015/0250937 A1 | 9/2015 | Pudil |
| 2015/0251161 A1 | 9/2015 | Pudil |
| 2015/0251162 A1 | 9/2015 | Pudil |
| 2015/0258266 A1 | 9/2015 | Merchant |
| 2015/0306292 A1 | 10/2015 | Pudil |
| 2015/0367051 A1 | 12/2015 | Gerber |
| 2015/0367052 A1 | 12/2015 | Gerber |
| 2015/0367055 A1 | 12/2015 | Pudil |
| 2015/0367056 A1 | 12/2015 | Gerber |
| 2015/0367057 A1 | 12/2015 | Gerber |
| 2015/0367058 A1 | 12/2015 | Gerber |
| 2015/0367059 A1 | 12/2015 | Gerber |
| 2015/0367060 A1 | 12/2015 | Gerber |
| 2016/0236188 A1 | 8/2016 | Menon |
| 2016/0243540 A1 | 8/2016 | Menon |
| 2016/0243541 A1 | 8/2016 | Menon |

FOREIGN PATENT DOCUMENTS

| | | |
|---|---|---|
| CN | 103402563 A | 11/2013 |
| CN | 104936633 | 9/2015 |
| CN | 105658326 A | 6/2016 |
| DE | 102011052188 | 1/2013 |
| EP | 0264695 | 4/1988 |
| EP | 711182 B1 | 6/2003 |
| EP | 1701752 A2 | 9/2006 |
| EP | 1991289 | 11/2008 |
| EP | 1592494 B1 | 6/2009 |
| EP | 2575827 A2 | 12/2010 |
| EP | 2576453 A2 | 12/2011 |
| EP | 2446908 | 5/2012 |
| EP | 1545652 B1 | 1/2013 |
| EP | 1345856 B1 | 3/2013 |
| EP | 2344220 B1 | 4/2013 |
| EP | 1345687 | 6/2013 |
| JP | S5070281 A | 6/1975 |
| JP | S51-55193 | 5/1976 |
| JP | S51-131393 | 11/1976 |
| JP | S61164562 | 7/1986 |
| JP | 2981573 | 11/1999 |
| JP | 2005511250 | 4/2005 |
| JP | H4-90963 | 5/2005 |
| JP | 2007-44602 A | 2/2007 |
| JP | 200744602 | 2/2007 |
| JP | 200744602 A | 2/2007 |
| JP | 2013502987 | 10/2013 |
| WO | 9532010 A1 | 11/1995 |
| WO | 0057935 | 10/2000 |
| WO | 0185295 A2 | 11/2001 |
| WO | 2002043859 | 6/2002 |
| WO | 2003043677 A2 | 5/2003 |
| WO | WO 2003041764 | 5/2003 |
| WO | 2003051422 A2 | 6/2003 |
| WO | 2004064616 A2 | 8/2004 |
| WO | 2004062710 A3 | 10/2004 |
| WO | WO 2005/062973 A3 | 7/2005 |
| WO | 2005123230 A2 | 12/2005 |
| WO | 2007089855 A2 | 8/2007 |
| WO | WO 20070103411 | 9/2007 |
| WO | 2008075951 A1 | 6/2008 |
| WO | 2009157877 A1 | 12/2009 |
| WO | 2009157878 A1 | 12/2009 |
| WO | 20090157877 | 12/2009 |
| WO | 2010028860 A1 | 3/2010 |
| WO | 2010102190 A4 | 11/2010 |
| WO | 2010141949 | 12/2010 |
| WO | WO 2011/017215 | 2/2011 |
| WO | 2013019179 | 2/2013 |
| WO | 2013019179 A1 | 2/2013 |
| WO | 2013025957 | 2/2013 |
| WO | 2013027214 | 2/2013 |
| WO | 2013028809 | 2/2013 |
| WO | 2013028809 A3 | 2/2013 |
| WO | WO 2013/019179 | 2/2013 |
| WO | WO 2013/019994 | 2/2013 |
| WO | WO 2013-025957 | 2/2013 |
| WO | WO 2013/028809 | 2/2013 |
| WO | WO 2013-028809 | 2/2013 |
| WO | WO 2013019179 | 2/2013 |
| WO | WO2014121238 A1 | 2/2013 |
| WO | 2013019994 A3 | 4/2013 |
| WO | 2012060700 | 5/2013 |
| WO | 2013025844 A3 | 5/2013 |
| WO | 2013101888 | 7/2013 |
| WO | 2013103607 A1 | 7/2013 |
| WO | 2013103906 | 7/2013 |
| WO | WO 2013/103607 | 7/2013 |
| WO | WO 2013109922 | 7/2013 |
| WO | 2015060914 | 4/2015 |
| WO | WO 2015/080895 | 4/2015 |
| WO | WO 2015060914 | 4/2015 |
| WO | WO 2015/126879 | 8/2015 |
| WO | 2015142624 | 9/2015 |
| WO | 2015199764 | 12/2015 |
| WO | 2015199765 | 12/2015 |
| WO | 2015199863 | 12/2015 |
| WO | 2015199864 | 12/2015 |
| WO | WO 2015-199863 | 12/2015 |

(56) References Cited

FOREIGN PATENT DOCUMENTS

| WO | WO 2015-199864 | 12/2015 |
|---|---|---|
| WO | WO 2015199765 | 12/2015 |
| WO | WO 2016/191039 | 12/2016 |

OTHER PUBLICATIONS

[NPL245] U.S. Appl. No. 14/240,129, filed Aug. 22, 2013.
[NPL247] U.S. Appl. No. 13/835,735, filed Mar. 15, 2013.
[NPL2] PCT/US2015/032492 International Search Report dated Nov. 19, 2015.
[NPL3] PCT/US2015/019901 International Search Report and Written Opinion dated Jun. 5, 2015.
[NPL494] John Wm Agar: Review: Understanding sorbent dialysis systems, Nephrology, vol. 15, No. 4, Jun. 1, 2010, pp. 406-411.
[NPL4] PCT/US2015/016270 International Search Report and Written Opinion dated Jun. 5, 2015.
[NPL518] Office Action in U.S. Appl. No. 14/269,589, dated Nov. 4, 2016.
[NPL519] Office Action in U.S. Appl. No. 13/586,824 dated Dec. 21, 2015.
[NPL520] Office Action in U.S. Appl. No. 13/586,824 dated Jun. 4, 2015.
[NPL548] PCT/US15/18587 International Preliminary Report on Patentability dated Jun. 6, 2016.
[NPL550] European Search Opinion for App. No. EP12826180 dated Mar. 19, 2015.
[NPL551] European Search Opinion for App. No. EP12826180 dated Jan. 18, 2016.
[NPL584] Office Action in App. No. AU 2015280604 dated Apr. 8, 2016.
[NPL590] PCT/US2016/030319 Written Opinion dated Jul. 27, 2016.
[NPL591] PCT/US2016/030320 Written Opinion dated Jul. 27, 2016.
[NPL5] PCT/US2015/016273 International Search Report and Written Opinion dated Jun. 9, 2015.
[NPL601] Wester et al., A regenerable postassium and phosphate sorbent system to enhance dialysis efficacy and device portability: an in vitro study Nephrol Dial Transplant (2013) 28: 2364-2371 Jul. 3, 2013.
[NPL602] Office Action in App. No. JP 2016-515476 dated Dec. 26, 2016.
[NPL603] Japanese Patent Publication No. S50-70281A.
[NPL605] PCT/US2015/032494 Written Opinion dated Nov. 19, 2015.
[NPL606] PCT/US2015/032494 International Search Report dated Nov. 19, 2015.
[NPL607] PCT/US2015/019901 International Preliminary Report on Patentability dated May 27, 2016.
[NPL608] PCT/US2015/019901 Written Opinion dated May 27, 2016.
[NPL609] PCT/US2015/019901 Written Opinion dated Jun. 5, 2015.
[NPL610] PCT/US2015/019901 International Search Report dated Jun. 5, 2015.
[NPL611] PCT/US2015/032485 International Preliminary Report on Patentability dated May 11, 2016.
[NPL612] PCT/US2015/032485 International Preliminary Report on Patentability dated May 11, 2016.
[NPL613] PCT/US20115/032485 International Preliminary Report on Patentability dated May 11, 2016.
[NPL614] PCT/US2016/030304 International Search Report dated Jul. 27, 2016.
[NPL615] PCT/US2016/030304 Written Opinion dated Jul. 27, 2016.
[NPL616] PCT/US2016/030312 Written Opinion dated Jul. 28, 2016.
[NPL617] PCT/US2016/030312 International Search Report dated Jul. 28, 2016.
[NPL618] PCT/US2016/030319 International Search Report dated Jul. 27, 2016.
[NPL619] PCT/US2016/030319 Written Opinion dated Jul. 27, 2016.
[NPL620] PCT/US2016/030320 Written Opinion dated Jul. 28, 2016.
[NPL621] PCT/US2016/030320 International Search Report dated Jul. 28, 2016.
[NPL622] PCT/US2015/032485 Written Opinion dated Oct. 16, 2015.
[NPL623] PCT/US2015/032485 Written Opinion dated Oct. 16, 2016.
[NPL626] PCT/US2015/032485 International Search Report and Written Opinion dated Oct. 16, 2015.
[NPL634] PCT/US2016/030320 International Preliminary Report on Patentability, dated Apr. 20, 2017.
[NPL681] PCT/US2015/020047 International Search Report and Written Opinion dated Jun. 29, 2015.
[NPL682] PCT/US2015/020047 International Preliminary Report on Patentability dated Jun. 30, 2015.
[NPL684] PCT/US2015/020044 Written Opinion dated Jun. 21, 2016.
[NPL685] PCT/US2015/020044 International Preliminary Report on Patentability dated Nov. 4, 2016.
[NPL686] PCT/US2015/020044 International Search Report dated Jun. 30, 2015.
[NPL688] US2015/019881 Written Opinion dated Jun. 16, 2016.
[NPL689] US2015/019881 Written Opinion dated May 9, 2016.
[NPL690] US2015/019881 International Search Report and Written Opinion dated Jun. 29, 2015.
[NPL692] PCT/US2014/065950 International Preliminary Report on Patentability dated Oct. 28, 2015.
[NPL696] PCT/US2015/032485 Written Opinion dated May 9, 2016.
[NPL6] PCT/US2015/032492 Written Opinion dated Nov. 19, 2015.
[NPL720] PCT/US2015/019901 International Search Report and Written Opinion dated Jun. 5, 2015.
[NPL721] PCT/US2015/019901 International Preliminary Report on Patentability dated May 27, 2016.
[NPL722] PCT/US2015/032494 International Preliminary Report on Patentablity dated Dec. 27, 2016.
[NPL730] Office Action for Chinese Application No. 201580009562.5 dated Jul. 3, 2017.
[NPL734] International Preliminary Report on Patentability for Application No. PCT/US2015/032492 dated Jun. 30, 2017.
[NPL737] International Preliminary Report on Patentability for Application No. PCT/US2015/016273 dated Feb. 19, 2016.
[NPL747] European Search Report for App. No. 15751391.2 dated Aug. 4, 2017.
[NPL755] European Search Report and supplementary Search Report for App. No. 14865374.4 dated Jun. 12, 2017.
[NPL756] European Search Report and Supplemental Search Report in European Application No. 14865374.4 dated Jun. 12, 2017.
[NPL7] PCT/US2015/020046 International Search Report and Written Opinion dated Jun. 29, 2015.
[NPL8] PCT/US2015/020044 International Search Report Written Opinion dated Jun. 30, 2015.
[NPL] European Search Report App 14865374.4, dated Jun. 12, 2017.
Chinese Office Action in App. No. 201580009563.X, dated Mar. 13, 2018.
European Search Report for App. No. 15812081.6, dated Mar. 8, 2018.
European Search Report for App. No. 18153940.4, dated Jun. 12, 2018.
European Search Report for EP 15811439, dated Feb. 15, 2018.
European Search Report for EP App. No. 15810804.3, dated Feb. 15, 2018.
European Search Report for EP App. No. 15811326.6, dated Feb. 14, 2018.
European Search Report for EP App. No. 15811573.3, dated Feb. 15, 2018.

(56) References Cited

OTHER PUBLICATIONS

European Search Report for EP App. No. 15812413.1, dated Feb. 2, 2018.
European Search Report in EP 15811454, dated Feb. 15, 2018.
European Search Report in EP 15812559.1, dated Jan. 31, 2018.
Office Action in Japanese Application No. 2016-553344, dated Apr. 24, 2018.
PCT/US2016/030304_IPRP.
PCT/US2016/030319_IPRP.
Search Report for EP App. No. 17203984.4, dated Mar. 29, 2018.
Search Report in EP App. No. 15752771, dated Nov. 22, 2017.
U.S. Appl. No. 14/637,606_OA.
U.S. Appl. No. 14/645,394_OA.
[NPL10] Wheaton, et al., Dowex Ion Exchange Resins—Fundamentals of Ion Exchange; Jun. 2000, pp. 1-9. http://www.dow.com/scripts/litorder.asp?filepath=liquidseps/pdfs/noreg/177-01837.pdf.
[NPL162] International Search Report from PCT/US2012/051946 dated Mar. 4, 2013.
[NPL163] U.S. Appl. No. 61/526,209.
[NPL1] PCT/US2014/065950 International Search Report and Written Opinion dated Feb. 24, 2015.
[NPL238] PCT Application, PCT/US20013/020404, filed Jan. 4, 2013.
[NPL240] U.S. Appl. No. 13/836,973, filed Mar. 15, 2013.
[NPL241] U.S. Appl. No. 14/259,655, filed Apr. 23, 2014.
[NPL242] U.S. Appl. No. 14/259,589, filed Apr. 23, 2014.
[NPL243] U.S. Appl. No. 13/757,693, filed Jan. 4, 2013.

* cited by examiner

FIG. 4
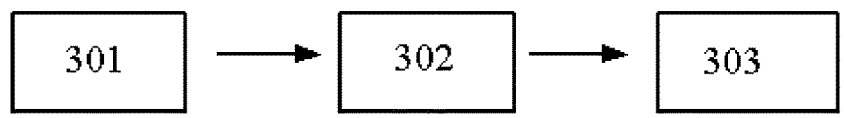
FIG. 5a       FIG.5b
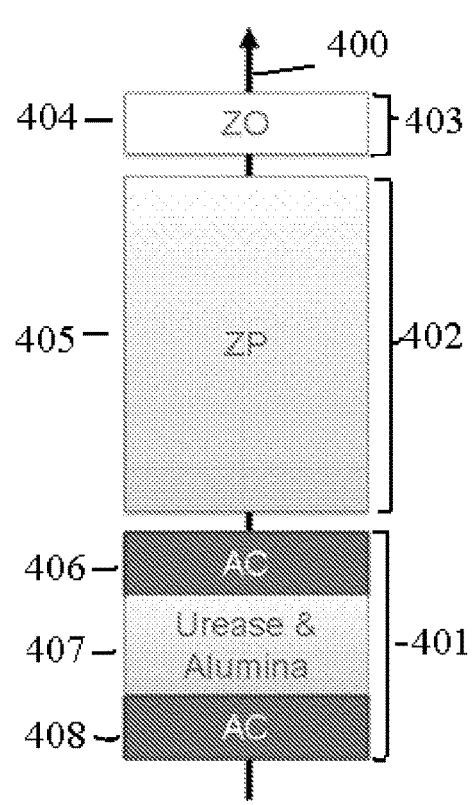
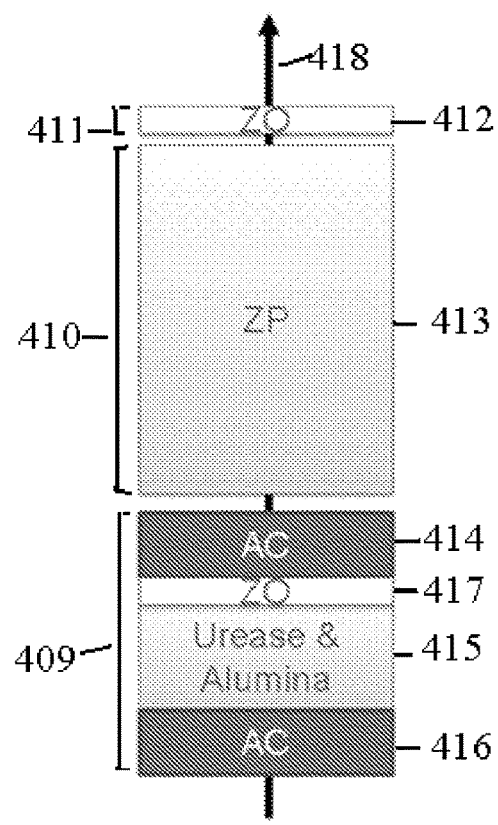

ZIRCONIUM PHOSPHATE RECHARGING METHOD AND APPARATUS

CROSS-REFERENCE

The present application is a Divisional of U.S. patent application Ser. No. 14/722,119 filed May 26, 2015, which is a continuation-in-part (CIP) application of U.S. patent application Ser. No. 14/642,847, filed Mar. 10, 2015, now U.S. Pat. No. 9,974,896, which claims priority to U.S. Provisional Application No. 62/077,159, filed Nov. 7, 2014, and U.S. Provisional Application No. 62/016,613, filed Jun. 24, 2014, the contents of each incorporated herein in their entirety by reference. The present invention is also a continuation-in-part (CIP) application of U.S. patent application Ser. No. 14/261,651, filed Apr. 25, 2014, now U.S. Pat. No. 9,895,477, which claims priority to U.S. Provisional Application No. 61/909,372, filed Nov. 26, 2013, and U.S. Provisional Application No. 61/941,672, filed Feb. 19, 2014, the contents of each incorporated herein in their entirety by reference.

FIELD OF THE INVENTION

The invention relates to a method and apparatus for sorbent recharging, and recharging zirconium phosphate, in particular. The method and related apparatus can recharge a specific rechargeable layer of a sorbent material in a sorbent cartridge or a sorbent module. Zirconium phosphate can be recharged by passing a solution or solutions through the zirconium phosphate wherein the solution(s) contain appropriate solutes for recharging the sorbent material. The solution can contain a combination of acid/buffer solution with each component at a specified concentration. The zirconium phosphate can be included in a sorbent cartridge or module, and the zirconium phosphate can be recharged without removing the zirconium phosphate from a sorbent cartridge. The recharge process can establish capacity of the zirconium phosphate for cation removal and provide a consistent predicable, pH profile during a therapy session.

BACKGROUND

Zirconium phosphate is a common material used in sorbent cartridges for sorbent dialysis. Zirconium phosphate can remove ammonium ions from spent dialysate, generated by the breakdown of urea in the spent dialysate by urease, as well as potassium, calcium, and magnesium ions from spent dialysate. Known sorbent dialysis systems generally require the sorbent materials to be discarded and the sorbent cartridge replaced after each use. Discarding and replacing of expensive sorbent materials, such as zirconium phosphate, increases both costs and waste.

Zirconium phosphate operates by exchanging sodium and/or hydrogen ions bound the zirconium phosphate for ammonium, potassium, calcium, magnesium and other cations present in spent dialysate. The ratio of sodium to hydrogen ions released by the zirconium phosphate into the dialysate may depend on the ratio originally bound to the zirconium phosphate. When the zirconium phosphate is recharged using acid solutions, neutralization is necessary in order for the zirconium phosphate to be reused in a dialysis session. Known sorbent dialysis systems do not provide a way to recharge the zirconium phosphate, wherein the additional neutralization is not necessary. Known sorbent dialysis systems do not provide for a way to recharge the zirconium phosphate present in a sorbent cartridge so that the zirconium phosphate can be reused for future dialysis sessions. Instead, known sorbent dialysis systems generally require the sorbent materials to be discarded and the sorbent cartridge replaced after each use. Although traditional sorbent cartridges can be broken down to extract the sorbent materials for recharging, the sorbent materials must be re-processed at a processing plant, and cannot be recharged by the dialysis machine, a recharging device, or an in-clinic apparatus. The exhausted sorbent materials must be transported to a processing plant, the sorbent cartridge disassembled and the sorbent materials recharged by the plant. At some point, a new cartridge must be manufactured and the recharged sorbent materials re-packaged into the cartridge and transported back to the dialysis clinic for use. Traditional cartridges also cannot isolate specific materials into compartments for recharging, and therefore, cannot be adapted to recharge expensive rechargeable sorbent materials. Single- and limited-use sorbent cartridges drive up not only the unit cost of dialysis, but also the total cost of dialysis.

As such, there is a need for systems and methods for recharging sorbent materials such as zirconium phosphate for reuse. There is also a need for methods and systems for separating sorbent materials within a sorbent cartridge into single and multi-use modules that can facilitate recharging and reuse of at least one of the sorbent materials. There is a further need for systems and related methods whereby rechargeable sorbent materials can be separated into multi-use modules and single-use modules wherein non-rechargeable sorbent materials can optionally be contained in the single-use modules. There is also a need for systems and methods wherein the recharge solutions can result in different ratios of sodium to hydrogen ions bound to the rechargeable sorbent material according to the needs of the patient. There is a need for a recharge process and apparatus that can establish capacity of the zirconium phosphate for cation removal and provide a consistent predicable, pH profile during a therapy session.

SUMMARY OF THE INVENTION

The first aspect of the invention relates to a recharger. In any embodiment of the first aspect of the invention, the recharger can have at least a fluid source configured to contain at least one recharging fluid wherein the fluid source can be fluidly connectable to at least one rechargeable sorbent module for use in sorbent dialysis, and a fluid flow path fluidly connecting the fluid source and the rechargeable sorbent module, wherein the recharging fluid flows from the fluid source into an inlet of the rechargeable sorbent module, and then out of an outlet of the rechargeable sorbent module in the fluid path.

In any embodiment of the first aspect of the invention, the recharger can be configured to releasably hold at least one rechargeable sorbent module and the rechargeable sorbent module can contain zirconium phosphate.

In any embodiment of the first aspect of the invention, the recharger can further comprise multiple fluid sources each containing at least one recharging fluid, wherein the recharging fluid flows from each of the fluid sources into the inlet of the rechargeable sorbent module, and then out of the outlet of the rechargeable sorbent module.

In any embodiment of the first aspect of the invention, the recharger can further have a mixer positioned in the fluid flow path in between the at least two fluid sources and the rechargeable sorbent module, such that the recharging fluid from each fluid source is mixed prior to the recharging fluid flowing into the rechargeable sorbent module. In any embodiment of the first aspect of the invention, the mixer can be a junction between two merging fluid streams.

In any embodiment of the first aspect of the invention, the recharger can further comprise a heater to heat the recharging fluid.

In any embodiment of the first aspect of the invention, the heater can heat the recharging fluid in the fluid source.

In any embodiment of the first aspect of the invention, the heater can be positioned in the fluid flow path between the fluid source and the rechargeable sorbent module, such that the recharging fluid flows from the fluid source, through the heater, and then into the rechargeable sorbent module.

In any embodiment of the first aspect of the invention, the recharger can further comprise a water source fluidly connected to the flow path, wherein water from the water source flows into the rechargeable sorbent module.

In any embodiment of the first aspect of the invention, the recharger can further comprise at least one sensor to measure a characteristic of the recharging fluid.

In any embodiment of the first aspect of the invention, the sensor can be a conductivity sensor.

In any embodiment of the first aspect of the invention, the fluid source can be a storage tank.

In any embodiment of the first aspect of the invention, the storage tank can contain the recharging fluid to recharge multiple rechargeable sorbent modules.

In any embodiment of the first aspect of the invention, the recharger can be configured to releasably hold at least one rechargeable sorbent module, the rechargeable sorbent module fluidly connectable to the fluid source.

In any embodiment of the first aspect of the invention, a first fluid source can contain a sodium salt, a second fluid source can contain a base and a third fluid source can contain an acid.

In any embodiment of the first aspect of the invention, the recharger can be any one of the following: a) the fluid source can contain sodium chloride, sodium acetate, and acetic acid; b) the recharger can comprise a first fluid source and a second fluid source, wherein the first fluid source contains sodium chloride and sodium acetate, and the second fluid source contains acetic acid; c) the recharger can comprise a first fluid source, a second fluid source, and a third fluid source, wherein the first fluid source contains a sodium salt, the second fluid source contains sodium hydroxide, and the third fluid source contains acetic acid; d) the recharger can comprise a first fluid source, a second fluid source, and a third fluid source, wherein the first fluid source contains a saturated solution of sodium chloride, the second fluid source contains a base, and the third fluid source contains an acid; e) the recharger comprises a first fluid source and a second fluid source, wherein the first fluid source contains sodium chloride and sodium diacetate and the second fluid source contains acetic acid; and f) the recharger comprises a first fluid source, a second fluid source, and a third fluid source, wherein the first fluid source contains a sodium salt, the second fluid source contains sodium acetate and the third fluid source contains acetic acid; and g) the recharger comprises a first fluid source, and a second fluid source, wherein the first fluid source contains a sodium salt and a base, and the second fluid source contains an acid.

In any embodiment of the first aspect of the invention, the recharger can comprise at least one pump to control the recharging fluid flowing from the fluid source into the fluid flow path.

In any embodiment of the first aspect of the invention, the recharger can further comprise a heat exchanger, the heat exchanger comprising at least two compartments, wherein the recharging fluid flows from the fluid source into a first compartment of the heat exchanger prior to entering the rechargeable sorbent module, and the to the recharging fluid flows into a second compartment of the heat exchanger after flowing out of the rechargeable module.

In any embodiment of the first aspect of the invention, the recharger can be configured to releasably hold at least one rechargeable sorbent module and the rechargeable sorbent module can contain zirconium oxide.

Any of the features disclosed above as being part of the first aspect of the invention can be included in the first aspect of the invention either alone or in combination.

The second aspect of the invention relates to a method of recharging zirconium phosphate. In any embodiment of the second aspect of the invention, the method can comprise passing a single solution through the zirconium phosphate for ion exchange, wherein passing the single solution through the zirconium phosphate results in zirconium phosphate that will maintain a substantially consistent pH in a dialysate used during dialysis.

In any embodiment of the second aspect of the invention, the single solution can comprise a sodium salt/buffer solution.

In any embodiment of the second aspect of the invention, the pH value of the single solution can be predetermined according to a pH profile desired during a next therapy session.

In any embodiment of the second aspect of the invention, the single solution can be generated through mixing a first solution having a predetermined sodium concentration and a second solution having a predetermined acid concentration.

In any embodiment of the second aspect of the invention, the first solution can consist essentially of sodium acetate and sodium chloride and the second solution can be an acetic acid solution.

In any embodiment of the second aspect of the invention, the first solution and the second solution each can be introduced into a mixer at a predetermined concentration.

In any embodiment of the second aspect of the invention, the method can further comprise controlling a temperature of the single solution.

In any embodiment of the second aspect of the invention, the temperature of the single solution is controlled by controlling a temperature of the first solution and the second solution prior to mixing.

In any embodiment of the second aspect of the invention, the temperature of the single solution can be controlled by controlling a heater to heat the solution after mixing.

In any embodiment of the second aspect of the invention, one or more components of the single solution can be contained in a single fluid source to provide for one or more rechargers in the recharging.

In any embodiment of the second aspect of the invention, a third solution can be mixed with the first solution and the second solution to generate the single solution for the recharging.

In any embodiment of the second aspect of the invention, the first and second solutions can be mixed in a recharger used for the recharging of the zirconium phosphate.

In any embodiment of the second aspect of the invention, at least one of conductivity and pH of the single solution can be measured.

In any embodiment of the second aspect of the invention, can comprise adding an acid solution to the zirconium phosphate after the single solution passes through the zirconium phosphate.

In any embodiment of the second aspect of the invention, the zirconium phosphate can be contained in a sorbent cartridge for use in sorbent dialysis.

In any embodiment of the second aspect of the invention, the reusable module can be detachable from the sorbent cartridge.

In any embodiment of the second aspect of the invention, the reusable module can further contain zirconium oxide.

In any embodiment of the second aspect of the invention, the method can be carried out using a recharger.

Any of the features disclosed above as being part of the second aspect of the invention can be included in the first aspect of the invention either alone or in combination.

The third aspect of the invention is related to a solution for recharging zirconium phosphate. In any embodiment of the third aspect of the invention, the solution can comprise a combination of at least one sodium salt and at least one acid, the solution having a predetermined pH value that results in a substantially consistent pH in a dialysate passing through the zirconium phosphate after the solution is used for recharging zirconium phosphate.

In any embodiment of the third aspect of the invention, the solution can be selected from the group consisting of sodium acetate/acetic acid solution, glycolic/glycolate solution, citric/citrate solution, propionate/propionic solution, phosphoric/phosphate solution, or any combination thereof.

In any embodiment of the third aspect of the invention, the solution can consist essentially of sodium chloride, sodium acetate and acetic acid.

In any embodiment of the third aspect of the invention, concentrations of the sodium chloride, the sodium acetate, and the acetic acid can be about 3.60M, 0.40M, and 0.40M, respectively, or about 3.88M, 0.12M, and 0.40M, respectively.

Any of the features disclosed above as being part of the third aspect of the invention can be included in the first aspect of the invention either alone or in combination.

BRIEF DESCRIPTION OF THE DRAWINGS

FIG. 4 shows representative steps for a recharging process of a rechargeable material, such as zirconium phosphate.

FIGS. 5a and 5b show examples of a sorbent cartridge having rechargeable materials in multi-use and single-use modules.

DETAILED DESCRIPTION OF THE INVENTION

Figure 1:
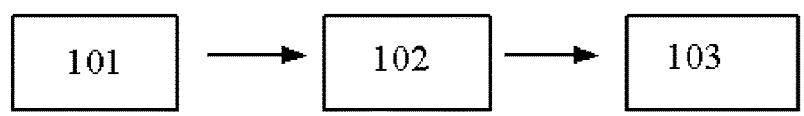
FIG. 1 shows a flow diagram of representative steps for the method of the invention.

Unless defined otherwise, all technical and scientific terms used herein generally have the same meaning as commonly understood by one of ordinary skill in the relevant art.

The articles "a" and "an" are used herein to refer to one or to more than one (i.e., to at least one) of the grammatical object of the article. By way of example, "an element" means one element or more than one element.

An "acid" as used herein can be either a Lewis acid or a Brønsted-Lowry acid. A Lewis acid is a compound that is capable of accepting a lone pair of electrons. A Brønsted-Lowry acid is a compound that is capable of donating a hydrogen ion to another compound.

A "base" as used herein can be either a Lewis base or a Brønsted-Lowry base. A Lewis acid is a compound that is capable of donating a lone pair of electrons. A Brønsted-Lowry base is a compound that is capable of accepting a hydrogen ion from another compound.

A "buffer solution" is a solution comprising a weak acid and the conjugate base of the weak acid.

The term "cartridge" refers to any container designed to contain a powder, fluid, or gas made for ready connection to a device, structure, system, flow path, or mechanism. The container can have one or more compartments. Instead of compartments, the container can also be comprised of a system of two or more modules connected together to form the cartridge wherein the two or more modules once formed can be connected to a device, structure, system, flow path, or mechanism.

The term "characteristic" of a fluid refers to any variable of a fluid that can be measured or described. Characteristics of fluid include, but are not limited to, conductivity, pH, temperature, and concentrations of one or more solutes.

"Clean" or "cleaning" refers to the process of removing impurities, toxins or biological material, such as by killing or rendering nonviable any bacteria, virus, fungus or other biologic material.

A "compartment" is a portion of a component or container that is physically separated from another portion of the component or container.

The term "comprising" includes, but is not limited to, whatever follows the word "comprising." Thus, use of the term indicates that the listed elements are required or mandatory but that other elements are optional and may or may not be present.

A "conductivity sensor" is a sensor configured to measure the conductivity of a fluid.

The term "configured to contain" means any particular form, alignment, shape, design, marking, or arrangement suitable for an intended material to be contained therein. "Conjugate base" refers to the compound formed after an acid donates a hydrogen ion to another compound.

The term "consisting of" includes and is limited to whatever follows the phrase "consisting of" Thus, the phrase indicates that the limited elements are required or mandatory and that no other elements may be present. The term "consisting essentially of" includes whatever follows the term "consisting essentially of" and additional elements, structures, acts or features that do not affect the basic operation of the apparatus, structure or method described.

The term "contain" as used herein means to keep a material within a specific place. "Contain" can refer to materials that are placed within a component, absorbed onto a component, bound to a component, or any other method of keeping the material in a specific place.

The term "container" as used herein is a receptacle that may be flexible or inflexible for holding any fluid or solid, such as for example a spent dialysate fluid, or a sodium chloride or sodium bicarbonate solution or solid, or urease, or urease/alumina, and the like. A "sorbent container" is any receptacle configured to hold one or more sorbent materials. Similarly, a "urease container" is any receptacle configured to hold urease.

The terms "detachable," "detached," or "detachably" relate to any component of the present invention that can be separated from a system, module, cartridge or any component of the invention. "Detachable" can also refer to a component that can be taken out of a larger system with minimal time or effort. In certain instances, the components can be detached with minimal time or effort, but in other instances can require additional effort. The detached component can be optionally reattached to the system, module, cartridge or other component. A detachable module can often be part of a reusable module.

"Dialysate" is the fluid that passes through the dialyzer on the side of the dialysis membrane that is opposite to the fluid (e.g. blood) that is being dialyzed.

"Dialysate regeneration" refers to the process of treating spent dialysate, containing solutes removed from the patient's blood, with one or more sorbent materials in order to remove specific solutes, such as urea, and thereby generate dialysate that can be reused for dialysis.

"Dialysis" is a type of filtration, or a process of selective diffusion through a membrane. Dialysis removes solutes of a specific range of molecular weights via diffusion through a membrane from a fluid to be dialyzed into a dialysate. During dialysis, a fluid to be dialyzed is passed over a filter membrane, while dialysate is passed over the other side of that membrane. Dissolved solutes are transported across the filter membrane by diffusion between the fluids. The dialysate is used to remove solutes from the fluid to be dialyzed. The dialysate can also provide enrichment to the other fluid.

A "dialysis flow path" is the route in which a fluid will travel during dialysis.

A "dialysis session" refers to the medical procedure wherein dialysis is preformed on a patient.

The term "dialyzer" refers to a cartridge or container with two flow paths separated by semi-permeable membranes. One flow path is for blood and one flow path is for dialysate. The membranes can be in the form of hollow fibers, flat sheets, or spiral wound or other conventional forms known to those of skill in the art. Membranes can be selected from the following materials of polysulfone, polyethersulfone, poly(methyl methacrylate), modified cellulose, or other materials known to those skilled in the art.

"Draining" refers to the process of removing a fluid from a component.

"Flow" refers to the movement of a fluid or a gas.

The term "flow path" refers to a grouping of components that may guide the movement of a fluid, convey the fluid, exchange energy with the fluid, modify the composition of the fluid, measure a characteristic of the fluid and/or detect the fluid. A flow path comprises a route or a collection of routes for a fluid to move within. Within a flow path there may be more than one route that a volume of fluid can follow to move from one position to another position. A fluid volume may move through a flow path such that the fluid volume recirculates, or passes the same position more than once as the fluid volume moves through a flow path. A flow path may operate to cause fluid volume ingress to and fluid volume egress from the flow path.

A "fluid" is a liquid substance optionally having a combination of gas and liquid phases in the fluid. Notably, a liquid, as used herein, can therefore also have a mixture of gas and liquid phases of matter.

A "fluid source" is a source from which at least one fluid can be obtained. The fluid source can be a tank containing a fluid, a mixer into which multiple fluids can be added and mixed, a dedicated fluid line, such as a municipal water line, or any other source from which a fluid can be obtained.

The term "fluid communication" refers to the ability of fluid or gas to move from one component or compartment to another within a system or the state of being connected, such that fluid or gas can move by pressure differences from one portion that is connected to another portion.

The term "fluidly connectable," "fluidly connect," and the like, refer to the ability of providing for the passage of fluid or gas from one point to another point. The two points can be within or between any one or more of compartments, modules, systems, components, and rechargers, all of any type.

"Functional capacity" is the ability of a material to accomplish the material's intended function. In some instances functional capacity can refer to the ability of a sorbent material to remove specific ions from a fluid, or to transform specific solutes into other materials.

A "heater" is a device capable of heating a fluid or gas.

A "heat exchanger" is a device comprising at least two compartments, wherein a fluid or gas can pass through one compartment, while a second fluid or gas can pass through the second compartment. Heat transfer occurs between the two compartments of the heat exchanger, such that if the fluids or gases in opposite compartments are at different temperatures, the higher temperature fluid or gas will act to heat up the lower temperature fluid or gas.

An "inlet of a sorbent module" refers to a fluid connector on the sorbent module, where the fluid can pass through the connector and flow into the sorbent module.

"Ion exchange" refers to the exchange of one ion on a material or in a fluid for a second ion on a material or in a fluid.

The term "ions carried" by a material refers to the amount or type of ions that have been adsorbed, absorbed or otherwise attached to the material.

The term "measure" means to determine values of one or more variables of a system or material.

The term "merging fluid streams" refers to a position in a flow path where one stream of fluid contacts another stream of fluid, resulting in a single stream of fluid that is a combination of the two original fluid streams.

A "mixer" is a component configured to receive fluids from multiple sources and to mix the fluids together. In any embodiment, a mixer may include components that agitate the fluids to further the mixing. In any embodiment a mixer may be a junction between multiple merging fluid streams, wherein the merging of the fluid streams provides mixing of the fluid streams.

"Module" refers to a discreet component of a system. Each of the modules can be fitted to each other to form a system of two or more modules. Once fitted together, the modules can be in fluid connection and resist inadvertent disconnection. A single module can represent a cartridge to be fitted to a device or mechanism if the module is designed to contain all the necessary components for an intended purpose such as a sorbent for use in dialysis. In such a case, the module can be comprised of one or more compartments within the module. Alternatively, two or more modules can form a cartridge to be fitted to a device or mechanism where each module individually carries separate components but only when connected together contain in summation all the necessary components for an intended purpose such as a sorbent for use in dialysis. A module can be referred to as a "first module," "second module," "third module," etc. to refer to any number of modules. The designation of "first," "second," "third," etc. does not refer to the respective placement of the module in the direction of fluid or gas flow, and merely serves to distinguish one module from another unless otherwise indicated.

A "multi-use module" or a "reusable module" is a module that can be used for more than one dialysis session, often with recharging of the sorbent materials inside the module between uses.

An "outlet of a sorbent module" refers to a fluid connector on the sorbent module, such that the fluid received by or stored in the sorbent module flows out of the sorbent module through the connector.

The term "on-line feed" refers to supplying a material, such as a fluid to a flow path of a same or different fluid.

The term "passing a solution through" a component refers to the solution entering the component, moving through at least part of the interior of the component, and then exiting the component.

The terms "pathway," "conveyance pathway," "fluid flow path," and "flow path" refer to the route through which a fluid or a gas, such as dialysate or blood, travels, or the route a gas travels.

The term "pump" refers to any device that causes the movement of fluids or gases by applying suction or pressure.

A "recharger" refers to an apparatus designed to recharge at least one material.

"Recharging" refers to the process of treating a sorbent material to restore the functional capacity of the sorbent material so as to put the sorbent material back into a condition for reuse or use in a new dialysis session. In some instances, the total mass, weight and/or amount of "rechargeable" sorbent materials remain the same. In some instances, the total mass, weight and/or amount of "rechargeable" sorbent materials change. Without being limited to any one theory of invention, the recharging process may involve exchanging ions bound to the sorbent material with different ions, which in some instances may increase or decrease the total mass of the system. However, the total amount of the sorbent material will in some instances be unchanged by the recharging process. Upon a sorbent material undergoing "recharging," the sorbent material can then be said to be "recharged." Recharging of rechargeable sorbent materials is not the same as replenishing of a particular sorbent material such as urease. Notably, urease is not generally "recharged," but can be replenished, as defined herein.

A "recharging fluid" is a fluid comprising the appropriate ions for recharging a specific sorbent material.

A "recharging solution" or a "recharge solution" is a solution comprising the appropriate ions for recharging a specific sorbent material.

A "recharging solution source" is a source of a recharging solution as defined herein. The recharging solution source can be a tank containing a recharging solution, a mixer into which multiple components of a recharging solution can be added and mixed, or any other source from which a recharging solution can be obtained.

The term "releasably hold" refers to the ability to keep a component in a particular place or position, where the component can be removed from that place or position.

"Replenishing" means to add back into a system, section or module, a material that was previously removed, reduced, depleted, or taken out from that system, section or module. For example, after introducing an amount of a sorbent material, e.g., urease, that was reduced in quantity and/or functional capacity in a compartment, the compartment with the freshly introduced sorbent material can then be said to be "replenished."

"Reusable" or "reusing" refers in one instance to a solid, liquid, gas that can be used more than one time, optionally with treatment of any type of the material between uses. For example, a material and a solution can be reused. In one instance, reusable can refer to a cartridge, as used herein, that contains a material that can be recharged by recharging the material(s) contained within the cartridge.

"Rinsing" refers to passing a fluid, such as water, through a component in order to remove a fluid or solid previously in the component.

"Saturated" refers to a solution containing the maximum possible amount of a particular solute at a given temperature.

A "section" refers to any portion of a larger component. A section can be referred to as a "first section," "second section," "third section," etc. to refer to any number of sections. The designation of "first," "second," "third," etc. does not refer to the respective placement of the section in the direction of fluid or gas flow, and merely serves to distinguish one section from another unless otherwise indicated. Additionally, each section can be optionally physically separated such as by a divider or wall; however, referring to a particular section does not necessarily require physical separation and merely refer to a particular location in which a material is contained.

A "sensor" is a component capable of determining the states of one or more variables in a system.

A "single-use module" is a module that contains sorbent materials that are not intended to be recharged. A "single-use" module can be used more than one time, but requires replenishing or refilling of the sorbent materials inside.

A "sodium salt" is an ionic compound made up of at least one sodium ion and at least one anion, wherein the ratio of sodium ions to anions is based on the charge of the anion, in order to achieve an electrically neutral compound.

A "solution," as used herein is a homogeneous mixture comprising a solvent and at least one solute, wherein the solute is dissolved in the solvent.

"Sorbent cartridge" refers to a cartridge that can contain one or more sorbent materials. The cartridge can be connected to a dialysis flow path. The sorbent materials in the sorbent cartridge are used for removing specific solutes from solution, such as urea. The sorbent cartridge can have a single compartmental design wherein all sorbent materials necessary for performing dialysis are contained within the single compartment. Alternatively, the sorbent cartridge can have a modular design wherein the sorbent materials are dispersed across at least two different modules, which can be connected to form a unitary body. Once the at least two modules are connected together, the connected modules can be referred to as a sorbent cartridge, which can be fitted to a device or mechanism. When a single module contains all the sorbent materials necessary for performing dialysis, the single module can be referred to as a sorbent cartridge.

A "sorbent cartridge module" means a discreet component of a sorbent cartridge. Multiple sorbent cartridge modules can be fitted together to form a sorbent cartridge of two or more sorbent cartridge modules. In some embodiments, a single sorbent cartridge module can contain all of the necessary materials for use in dialysis. In such cases, the sorbent cartridge module can be considered to be a "sorbent cartridge."

"Sorbent materials" are materials capable of removing specific solutes from solution, such as urea.

A "sorbent module" is a container containing at least one sorbent material. In some embodiments, the sorbent module can connect to another sorbent module to form a sorbent cartridge.

"Spent dialysate" is a dialysate contacted with blood through a dialysis membrane and contains one or more impurity, or waste species, or waste substance, such as urea.

A "storage tank" is a container that can contain a material, such as a fluid, for later use.

"Substantially consistent" means with little change during a process. A variable may be substantially consistent during a particular process with small changes in the value of the variable.

"Trace impurities" refers to a small amount of a compound or compounds present in an otherwise pure solution or material containing only specified compound or compounds.

A "valve" is a device capable of directing the flow of fluid or gas by opening, closing or obstructing one or more pathways to control whether or not the fluid or gas to travel in a particular path. One or more valves that accomplish a desired flow can be configured into a "valve assembly."

A "water source" is a fluid source as defined herein, from which water can be obtained.

The terms "waste species," "waste products," "waste," or "impurity species" refer to any molecular or ionic species originating from the patient or subject, including metabolic wastes, molecular or ionic species including nitrogen or sulfur atoms, mid-weight uremic wastes and nitrogenous waste. Waste species are kept within a specific homeostasis range by individuals with a healthy renal system.

Zirconium Phosphate Recharging

The first, second, and third aspects of the invention provide for methods and related apparatuses for recharging a rechargeable sorbent material. The rechargeable sorbent material can be selected from the group of zirconium phosphate, activated carbon, zirconium oxide, and other rechargeable sorbent materials as defined herein. The first, second, and third aspects of the invention provide for a method and apparatus for recharging zirconium phosphate used in dialysis systems that can displace any ammonium, potassium, calcium, magnesium, or other cations from the zirconium phosphate and replace them with sodium and/or hydrogen ions. By recharging the rechargeable sorbent material, and in particular, zirconium phosphate, in this manner, the rechargeable sorbent material, such as zirconium phosphate can be reused instead of discarded, reducing costs and waste. The rechargeable sorbent material such as zirconium phosphate may be part of a sorbent dialysis system. In particular, zirconium phosphate can be used to remove ammonium ions in spent dialysate generated by the breakdown of urea to ammonia and carbon dioxide by urease also present in the sorbent dialysis system. By recharging the zirconium phosphate after use, a sorbent cartridge or module containing the zirconium phosphate can also be reused more than once.

In any embodiment of the first, second or third aspects of the invention, a rechargeable sorbent material, such as zirconium phosphate, after processing a dialysate, may contain potassium, calcium, magnesium, ammonium, or other cations bound to the zirconium phosphate. Zirconium phosphate having reduced functional capacity can be recharged by a recharge solution as shown in the steps of FIG. 1. Specifically, at step 101 of FIG. 1, a recharge solution is prepared. The recharge solution can be a single solution containing a mixture of sodium/buffer solution, such as sodium chloride (NaCl), sodium acetate (NaAce), and acetic acid (HAce). Other buffer combinations can be used, for example, glycolic/glycolate solution, citric/citrate solution, propionate/propionic solution, monobasic phosphate, or any combination thereof. Sodium Monobasic phosphate may be particularly desirable, as sodium monobasic phosphate has a desired pH for recharging and allows for a single buffer component solution. Further, sodium monobasic phosphate is an odorless powder. For example, sodium monobasic phosphate can be used as a single buffer salt along with NaCl for recharge, where sodium monobasic phosphate may have a concentration between about 0 to 0.8 M, and NaCl may have a concentration between about 3.20 M to 4.00 M. The pH of the buffer solution containing sodium monobasic phosphate can be between any of about 2 and about 8, about 3 and about 5, about 3.5 and about 4.8, or about 4.0 and about 4.5. One skilled in the art will understand that further buffer combinations can be used. For example, the acid concentrate can include glycolic acid, because the amount to be added is lower and the cost has less impact for the systems of FIGS. 2B, 2E, and 2F. In addition, glycolic has no odor and is a solid, which may be beneficial in systems using a fluid source containing only an acid, as explained. At step 102, the recharge solution can be provided to pass through the zirconium phosphate, wherein ion exchange occurs between the zirconium phosphate and the recharge solution. The high sodium concentration in the recharge solution can displace the cations present in the zirconium phosphate and replace them with sodium ions. Hydrogen ions present in the solution can also displace cations present in the zirconium phosphate, resulting in zirconium phosphate with both sodium and hydrogen ions bound. The recharge solution leaving the zirconium phosphate can contain the displaced cations, along with any sodium and hydrogen ions that have not been bound to the zirconium phosphate. After the recharging process at step 102, the zirconium phosphate exists as a recharged zirconium phosphate, containing substantially sodium and hydrogen ions bound to the zirconium phosphate, in addition to some other trace impurities, if any, such as small amounts of cations that have not been displaced during recharging or impurities in the recharging solutions that have been bound to the zirconium phosphate. Trace impurities may not necessarily exist, and if present, may not necessarily affect the functional capacity of the rechargeable zirconium phosphate. In non-limiting examples, trace impurities such as undesired materials from the dialysate not subject to ion-exchanges may be removed by rinsing (not shown) using water or other solutions after the recharging step 102. In any embodiment of the first, second or third aspects of the invention, the recharged zirconium phosphate may meet any applicable standards for removal or limiting of trace impurities.

In any embodiment of the first, second or third aspects of the invention, the recharge solution used in step 102 of FIG. 1 can be a mixture of one or more sodium salts and acid. Non-limiting examples of sodium salt solutions that can be used include sodium chloride, sodium acetate, sodium citrate, sodium sulfate, sodium carbonate, sodium nitrate, or sodium phosphate. A person skilled in the art will understand that other sodium solutions can also be used to recharge the zirconium phosphate. When using a recharging solution that contains both an acid and a sodium salt, a recharged zirconium phosphate can also contain both hydrogen and sodium ions.

In any embodiment of the first, second, and third aspects of the invention, the ratio of sodium to hydrogen ions bound to the recharged zirconium phosphate can be customized for a particular patient, based on the patient's needs. The composition of sodium and hydrogen ions in the zirconium phosphate can influence the pH and the bicarbonate concentration leaving the sorbent cartridge and the amount of bicarbonate that may need to be added to the dialysate to achieve a desired bicarbonate concentration in the dialysate entering the dialyzer. This is because excess acid can react with the bicarbonate to form carbon dioxide. Based on the patient's starting urea and bicarbonate blood levels, a user can select the desired sodium and hydrogen composition in the zirconium phosphate that would achieve the appropriate dialysate bicarbonate composition required for the patient and minimize or eliminate the need for addition of bicarbonate into the dialysate.

The recharge solution can be a mixture of sodium salt and a buffer solution. A buffer solution can comprise a mixture of a weak acid and the conjugate base of the weak acid. An equilibrium can exist in a buffer solution between the relative concentrations of the acid and base. Adding or removing acid to the buffer solution causes a shift in the equilibrium. For example, removing hydrogen ions from the buffer solution, such as by binding the hydrogen ions to zirconium phosphate, will result in a shift in the equilibrium away from the base and towards the acid. As such, the buffer solution resists changes in pH because changes in $H^+$ concentration are compensated for by the shift in the acid/base equilibrium. The shift in equilibrium results in a solution having a substantially consistent pH during the recharging process, even as hydrogen ions are bound to the zirconium phosphate. Although small changes in pH may occur during the process, the pH of the solution remains substantially consistent due to the resistance of the buffer solution to pH changes. The pH of the buffer solution can be between any of about 4 and about 8, about 4.5 and about 6, about 6 and about 7, or about 5.5 and about 7.5. For example, a sodium/buffer solution may maintain pH value between about 3.5 and 4.8, or between about 4.0 and 4.5 during the recharging process. In non-limiting examples, the pH value of the recharge solution may not be necessarily measured during the recharging. The recharge solution may have a substantially consistent pH during the recharging. The recharge solution may not necessarily maintain a substantially consistent pH value during recharging.

A recharging solution having a buffer solution instead of only acid has a greater ability to control the hydrogen to sodium concentration in the recharged zirconium phosphate because the buffer provides greater control over the pH of the solution. Any buffer that can operate in the specific pH desired for the recharging process as explained herein can be used. Non-limiting examples include sodium acetate and acetic acid, sodium monobasic-phosphate and sodium dibasic-phosphate, and sodium citrate and citric acid.

In any embodiment of the first, second or third aspects of the invention, a lower pH will result in more hydrogen ions bound to the zirconium phosphate, while a higher pH will result in less hydrogen ions bound to the zirconium phosphate. The pH of the buffer solution can be between any of about 2 and about 8, about 3 and about 5, about 3.5 and about 4.8, or about 4.0 and about 4.5. When using a buffer solution as the recharge solution, fine-tuning of the sodium to hydrogen ion ratio can be done on the recharged zirconium phosphate by making changes in the pH and concentrations of the salt and buffer.

Table 1 shows a partial listing of possible recharge solutions containing a mixture of sodium chloride, sodium acetate, and acetic acid, where the sodium chloride can have a concentration between 3.20 M to 4.00 M, the sodium acetate can have a concentration between 0 M to 0.80 M, and the acetic acid can a concentration between 0.20 M to 0.80 M.

TABLE 1

Recharge solution compositions

| Recharge Solution | NaCl (M) | NaAce (M) | HAce (M) |
|---|---|---|---|
| 1 | 4.00 | 0.00 | 0.80 |
| 2 | 4.00 | 0.00 | 0.40 |
| 3 | 4.00 | 0.00 | 0.20 |
| 4 | 3.20 | 0.80 | 0.80 |
| 5 | 3.60 | 0.40 | 0.40 |
| 6 | 3.80 | 0.20 | 0.20 |
| 7 | 3.92 | 0.08 | 0.80 |
| 8 | 3.96 | 0.04 | 0.40 |
| 9 | 3.98 | 0.02 | 0.20 |
| 10 | 3.76 | 0.24 | 0.80 |
| 11 | 3.88 | 0.12 | 0.40 |
| 12 | 3.94 | 0.06 | 0.20 |

In any embodiment of the first, second or third aspects of the invention, the recharge solution can contain NaCl having a concentration of about 3.60 M, the NaAce having a concentration of about 0.40 M, and HAce having a concentration of about 0.40 M, such as solution 5 listed in Table 1. The recharge solution can also contain about 3.88 M NaCl, about 0.12 M NaAce, and about 0.40 M HAce, such as solution 11 listed in Table 1.

In any embodiment of the first, second, or third aspects of the invention, the recharge solution can result in a substantially consistent pH profile during therapy, such as the zirconium phosphate recharge solutions 5 and 11 listed in Table 1. The recharge solution that can result in zirconium phosphate capable of maintaining a substantially consistent pH profile of dialysate during therapy would provide greater control over the changes to the patient's blood pH during therapy.

In any embodiment of the first, second, or third aspects of the invention, the temperature for recharging zirconium phosphate can be any temperature between about 20° C. to 100° C. For example, the temperature can be any temperature between about 85° C. to 100° C. in a zirconium phosphate recharging process, as described. A lower temperature range may increase required time for preparing the readiness of reuse as the zirconium phosphate is recharged. In most cases, the temperature between 85° C.-100° C. is preferred for recharging the zirconium phosphate.

In non-limiting examples, the method of recharging the zirconium phosphate can also comprise a cleaning step after the single solution passes through the zirconium phosphate so as to clean the sorbent material so that the sorbent material can be stored and used in a subsequent dialysis session.

Recharge Solutions Delivery Process Flow Options

In any embodiment of the first, second, third, or fourth aspects of the invention, recharge solution can be delivered to a recharger for the recharging process of zirconium phosphate. A single recharge solution can be provided as a flow of premixed solution, which has desired concentrations of all essential components, for example, NaCl, NaAce, and HAce. The single recharge solution can be introduced to the one or more rechargers from a single fluid source, such as a storage tank. The single recharge solution can also be provided to one or more rechargers as two or more solutions containing separate components from two or more fluid sources, where the individual solutions can be mixed with each other inside the one or more rechargers.

In any embodiment of the first, second, or third aspects of the invention, the method of recharging the zirconium phosphate can further comprise a rinsing step using water before the single solution passes through the zirconium phosphate, when needed to rinse out the fluid lines of the recharger. For example, when a different recharge solution is provided to recharge a different rechargeable material. For example, NaOH solution, KOH solution, LiOH solution, or any other bases, can be provided as a recharge solution for zirconium oxide.

Before recharging the zirconium phosphate with the single recharge solution, rinsing of the fluid lines in the recharger may be necessary to clean out the basic solution used in recharging the zirconium oxide. In any embodiment of the first, second, or third aspects of the invention, the water feed can be used to rinse the zirconium phosphate after recharging the zirconium phosphate with the single recharge solution. Rinsing the zirconium phosphate after recharging can remove any residual acid, buffer or salt solutions from the zirconium phosphate prior to storage or reuse.

FIGS. 2a-2g show non-limiting examples of different options for delivering recharge solutions to one or more rechargers, which are denoted as the letter "R." In any embodiment of the first, second or third aspects of the invention, each of the one or more rechargers can recharge one or more rechargeable sorbent modules. The reusable or multi-use module can be configured to contain a rechargeable sorbent material, such as zirconium phosphate. The module can be of a size and shape suitable to hold an amount of zirconium phosphate necessary for a dialysis session. In any embodiment of the first or second aspects of the invention, the module can be labeled or color coded to indicate that the module is configured for containing zirconium phosphate. The module can include an RFID or barcode that, when scanned by a user, informs the user of the particular sorbent material that the module is configured to contain.

Figure 2A:
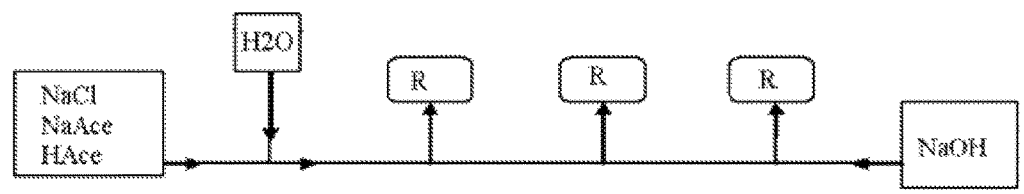
FIGS. 2a-2g show different configurations for preparing a zirconium phosphate recharge solution.

FIG. 2a shows a single brine tank as the fluid source, the brine tank containing a mixture of NaCl, NaAce, and HAce at desired concentrations as a single zirconium phosphate recharge solution. The recharge solution can be provided to one or more rechargers or to one or more sorbent modules on a single recharger. The brine tank can have varied volume to accommodate any number of rechargers and recharging runs per day. The tank volume could be sized for one recharger or for multiple rechargers, each of which can recharge one or more sorbent modules. The brine tank can be pre-heated to limit heating requirements on the rechargers. The brine tank can also include conductivity and/or pH sensors to ensure the correct composition of the recharge solution. In any embodiment of the first, second, or third aspects of the invention, the one or more rechargers can also be used for recharging other rechargeable materials, such as zirconium oxide, which can be rechargeable by NaOH. In any embodiment of the first, second, or third aspects of the invention, a water feed can be provided to rinse the recharging flow paths and to rinse the sorbent modules after recharging, and cool the sorbent modules after recharging and dilute the recharge solution if necessary. The water feed may also be used to dilute the concentrated recharge solution to the desired composition. A person skilled in the art will understand that the water feed can also be used to dilute one or more components of the recharge solution.

Figure 2B:
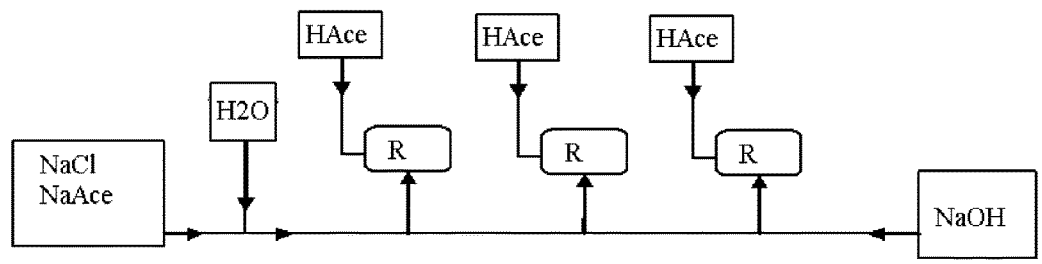

FIG. 2b shows a single brine tank as a first fluid source containing NaCl and NaAce at desired concentrations to supply one or more rechargers each configured to recharge one or more sorbent modules. The acetic acid can be provided separately from a second fluid source to each of the rechargers. NaCl and NaAce can be further mixed with HAce within each recharger to generate the final recharge solution having desired concentrations of the above components. The HAce can be fed to the flow path of the one or more components of the recharge solution, referred to as "on-line" feed. An on-line HAce feed can create the desired buffer solution, which can contain glacial HAce, for example at a concentration of 17M to limit volume. Varying HAce concentrations during a recharging process can be used. A second stage recharge step with straight acid can also be included to remove remaining materials not desired in the recharged zirconium phosphate. The on-line acetic acid can also be used to clean the rechargers, and may be safer compared to adding the acid to the brine tank.

A single tank containing a different recharge solution can be provided for recharging a different rechargeable material, for example, NaOH at desired concentration for zirconium oxide recharge. A water feed can be provided for rinsing the recharging flow paths in FIG. 2b and for rinsing the sorbent modules after recharging, cooling the sorbent module and for dilution of concentrated recharge solution.

The configuration of FIG. 2b can also include those described in FIG. 2a, such as tank volumes that can be varied to accommodate any number of rechargers and recharge runs per day. Correspondingly, the tank volume can be of a suitable size to performing recharging for the one or more rechargers. The brine tank may also include conductivity and/or pH sensors to ensure correct composition of the solution contained therein.

Figure 2C:
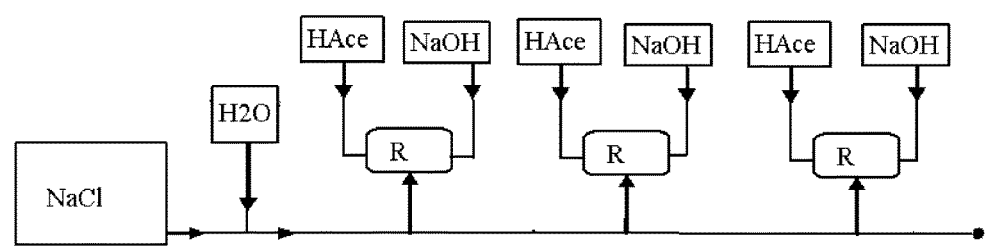

FIG. 2c shows a single brine tank containing NaCl at a desired concentration as a first fluid source, where an HAce feed and an NaOH feed are provided on-line to one or more rechargers as second and third fluid sources to create the desired buffer solution. For example, HAce and NaOH react to create an NaAce/HAce buffer. The configuration of FIG. 2c includes, but is not limited to, an on-line HAce feed and NaOH feed on a recharger to create the desired buffer solution containing glacial HAce (17M) and 50% NaOH (19M). To limit volume, NaOH can also be used to recharge zirconium oxide. Dilution of NaOH and neutralization with HAce can result in a temperature increase of ~10° C., which would reduce the load on the heater.

In FIG. 2c, any number of HAce concentration values can be used during a recharge. A straight acid can be added at a second recharge step to further remove undesirable components in the recharged zirconium phosphate. Moreover, the recharger can be cleaned with on-line acid and/or NaOH. Handling of acid may be safer compared to adding to the acid to the brine tank, and handling of NaOH may be safer compared to adding NaOH to a corresponding tank. The brine tank could be pre-heated to limit heating requirements on the recharger. In FIG. 2c, the tank volume can be varied to accommodate number of rechargers and recharge runs per day. The tank volume can be sized for one or more rechargers or for one or more modules. Tanks may also include conductivity and/or pH sensors to ensure correct composition of different solutions.

Figure 2D:
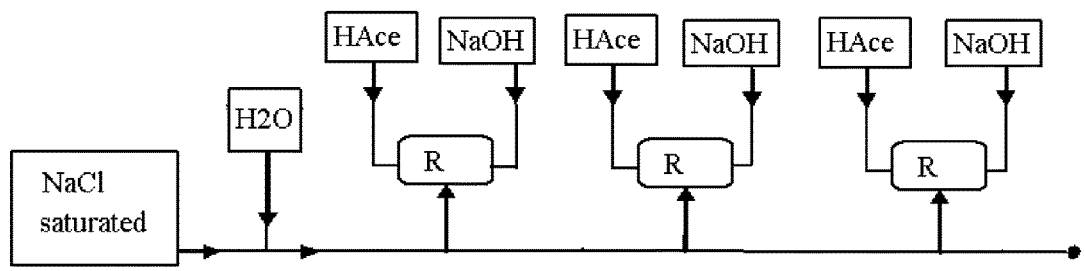

FIG. 2d is different than FIG. 2c in that the system shown in FIG. 2d utilizes a single brine tank as a first fluid source containing saturated NaCl for zirconium phosphate recharge, whereas FIG. 2c shows a single brine tank containing concentrated NaCl solution. FIG. 2d shows that a desired NaCl concentrate for recharge can be prepared by diluting the saturated NaCl with water on-line. A saturated brine tank can be easier to prepare than a brine tank having NaCl at a specific concentration. With a saturated brine tank as the fluid source, similar to a water softener tank, a user only needs to ensure the presence of insoluble NaCl. Also, the saturated brine tank can have a smaller volume. A person skilled in the art will understand that similar descriptions in FIG. 2c apply to FIG. 2d.

Figure 2E:
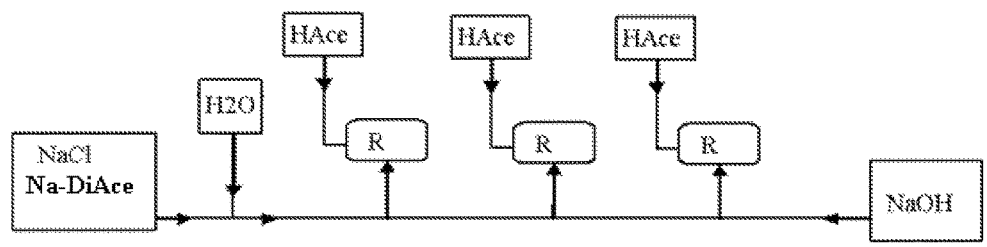

FIG. 2e shows a single brine tank as a first fluid source containing NaCl and sodium diacetate (Na-Diacetate) at desired concentrations for zirconium phosphate recharging. Na-Diacetate is equimolar NaAce and HAce. Na-Diacetate is a powder and may be easier to handle than liquid HAce. The delivery configuration of FIG. 2e is similar to the configuration of FIG. 2b, except for the use of Na-Diacetate. Similar descriptions regarding FIG. 2b apply to FIG. 2e.

Figure 2F:
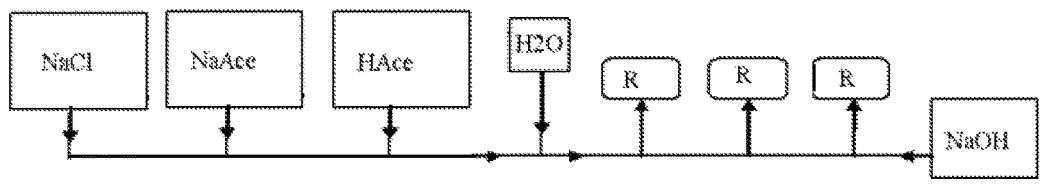

FIG. 2f shows individual tanks containing NaCl, NaAce, and HAce at desired concentrations for zirconium phosphate recharging as the fluid sources. The tanks can be preheated to limit heating requirements on the recharger, and can accommodate composition variation during recharge by controlling the relative amounts of fluid moved from each tank. Similar to the other options, the tank volumes in FIG. 2f can be varied to accommodate any number of rechargers and recharge runs per day, and can be sized for one or more rechargers. Each tank can include conductivity and/or pH sensors to ensure the correct recharge solution composition.

Figure 2G:
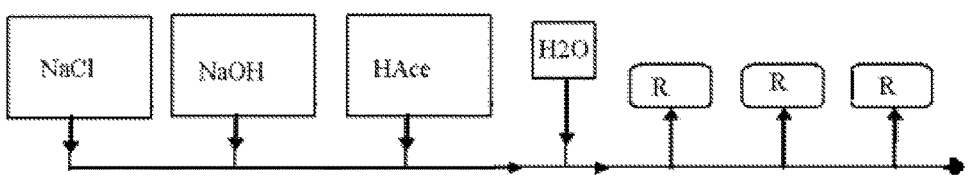

FIG. 2g shows individual tanks containing NaCl, NaOH, and HAce, respectively, at desired concentrations for zirconium phosphate recharge as the fluid sources. NaCl, NaOH, and H-Ace can be mixed together, and subsequently flow into each recharger. The delivery option in FIG. 2g can have the benefits listed for the option in FIG. 2c. Additionally, the option in FIG. 2g can reduce the number of fluid sources and other structures required for providing the recharge solution to each of the one or more rechargers, as compared to the option in FIG. 2c. The option in FIG. 2c shows each recharger being connected to a tank having NaOH and a different tank having HAce.

In any embodiment of the first, second or third aspects of the invention, the recharging solution can be mixed on-line or provided as a pre-mixed solution or any combination thereof, for the one or more rechargers. The pre-mixed solution can be stored in a container, such as a bag, a storage tank, or other container, for a user's convenience. The pre-mixed solution can contain any one or more components of the recharge solution. For example, the pre-mixed solution can contain a mixture of NaCl, NaOH, and HAce, or a mixture of NaCl and NaOH, or a solution of NaCl. The pre-mixed solution can be in either high or low concentrations. The pre-mixed solution can also be concentrated solutions, where water may be supplied for dilution in order to obtain the desired concentration.

Figure 3A:
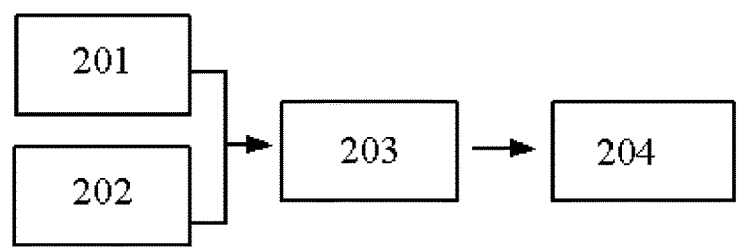
FIGS. 3a and 3b show representative steps and related devices for preparing a recharge solution from multiple fluid sources.

In any embodiment of first, second or third aspects of the invention, the recharge solution can be a mixture of a first solution from a first fluid source, such as a solution of NaAce and NaCl in a brine tank, referred to as a brine solution, and a second solution from a second fluid source, such as a solution of HAce in a different tank. In FIG. 3a, the first solution can be provided at step 201, and the second solution can be provided at step 202. The two solutions can be mixed together and heated at step 203, yielding a recharge solution for a rechargeable material, such as zirconium phosphate, at step 204.

Figure 3B:
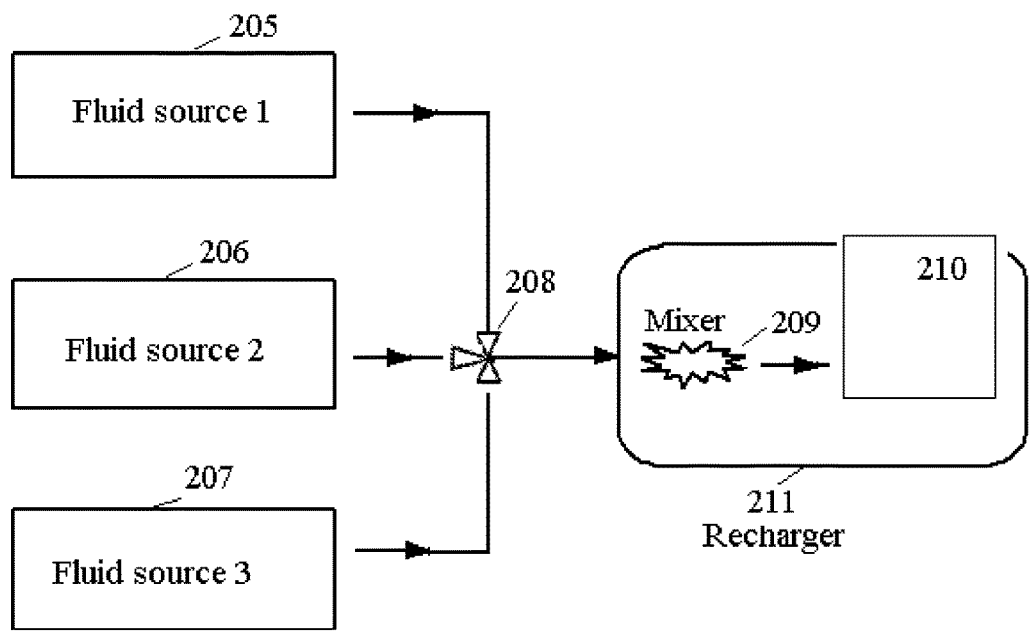

FIG. 3b shows that the first and second solutions can be mixed by a mixer 209 in a recharger 211. The first solution and second solution may come from any two of a first, a second, and a third fluid sources 205-207. The recharge solution may also be mixed by solutions from three different fluid sources. Solution from the fluid sources 205-207 can be controlled to flow into the recharger 211 through a three-way valve 208. The mixer 209 may be provided within the recharger 211 and may also be provided outside of the recharger 211. In non-limiting examples, the mixer 209 can be a junction of at least two merging streams, as could occur through a three-way connection or a four-way connection. The junction of the merging streams may provide adequate mixing for the merging streams. In non-limiting examples, the fluid from the fluid sources can flow into the recharger 211 via one or more inlets (not shown). The recharger 211 can have more than one mixer. The one or more mixers can be provided between the fluid resources 205-207 and the rechargeable material 210, such as zirconium phosphate. The valve 208 may be a three-way or four-way valve in order to associate with multiple fluid sources. A person skilled in the art will understand that the solutions may be provided as concentrated solutions and can be further diluted to reach the desired concentrations. Water can be provided from at least one of the fluid sources 205-207 or as an additional fluid source. The valve 208 can be controlled by a processor or the like (not shown) so that desired fluid can be released from the fluid sources 205-207 to the rechargeable material 210 via the mixer 209.

In a non-limiting example, the brine solution containing 0.95M NaAce and 3.28M NaCl is provided at 212 ml/min, 300 to 310 mS/cm at 25° C. for 30 minutes at step 201, and an acetic acid solution having 17.4 M Glacial H-Ace can be provided at 12 ml/min, 90-100 mS/cm at 25° C. for 30 minutes at step 202. The two solutions can be mixed together and heated up at step 203 to generate the final zirconium phosphate recharge solution.

Each of the variables of temperature, concentration and flow rate of the recharging solution can affect the amount of recharging solution necessary and the time necessary to recharge the zirconium phosphate. Each of these variables can be controlled independently depending on the needs and capabilities of the system. For example, if there is a need to conserve the recharging solution, a slower flow rate can be used with a higher temperature. In any embodiment of the first or second aspects of the invention, a zirconium phosphate recharge solution such as NaAce/HAce ranging from 0.01 to 3 M can be passed through a sorbent module containing zirconium phosphate weighing in a range from 0.01 to 5.0 kg. The temperature can be controlled to between 1 and 120° C., and include ranges such as 20 to 120° C., 30 to 120° C., 60 to 110° C., 85 to 100° C., 95 to 110° C., 75 to 110° C., or 50 to 100° C. Additionally, the flow rate of the recharging solution can be any one of 1 to 750 ml/min, 10 to 600 ml/min, 100 to 550 ml/min, 250 to 450 ml/min, 300 to 400 ml/min, 375 to 450 ml/min, 295 to 490 ml/min, 375 to 400 ml/min, or 300 to 500 ml/min. The conductivity of the recharging fluid can range from any one of 5 to 700 mS/cm, 10 to 700 mS/cm, 100 to 600 mS/cm, 200 to 500 mS/cm, 250 to 490 mS/cm, 300 to 400 mS/cm, 350 to 430 mS/cm, or 390 to 410 mS/cm where mS/cm (Siemens equal 1/ohms). The recharging time can range from 1-240, 2-45, 5-40, 10-60, 1-10, 1-30, 25-60, 15-30, or 10-30 minutes. The volume of recharging fluid can range from any one of 0.65 to 32.5 L, 1.55 to 30.5 L, 2.50 to 25.5 L, 3.5 to 30.5 L, 5.0 to 27.5 L, 6.5 to 32.5 L, or 6.5 to 12.5 L.

In one embodiment, a zirconium phosphate recharge solution can be passed through a sorbent module using a 0.9 M NaAce/H-Ace, 3.1M NaCl in a total volume of 6.73 L. The recharge solution can maintain a temperature of 85° C.-100° C. and pass through the zirconium phosphate at 224 ml/min and 390 to 410 mS/cm for 30 minutes at step 204. In another embodiment, the zirconium phosphate solution can be passed through a sorbent module using a 1.1 M NaAce/H-Ace, 3.2M NaCl in a total volume of 7.17 L. The recharge solution can maintain a temperature of 95° C.-110° C. and pass through the zirconium phosphate at 250 ml/min and 410 to 430 mS/cm for 40 minutes. In yet another embodiment, the zirconium phosphate solution can be passed through a sorbent module using a 1.3 M NaAce/H-Ace, 3.7 M NaCl in a total volume of 5.73 L. The recharge solution can maintain a temperature of 50° C.-90° C. and pass through the zirconium phosphate at 561 ml/min and 450 to 510 mS/cm for 20 minutes.

In any embodiment of the first, second or third aspects of the invention, a recharger can be used for multiple rechargeable materials or multiple modules containing different rechargeable materials, such as zirconium phosphate and zirconium oxide. For example, a recharger can be supplied with a recharging solution of zirconium phosphate as shown FIGS. 2c and 2d, as explained. A recharge solution containing mainly NaOH for recharging zirconium oxide by means of valves placed in the recharge solution flow path. The recharge solution for zirconium oxide could be any base. A base solution such as NaOH ranging from 0.1 to 5.0M can be passed through a sorbent module containing zirconium oxide weighing in a range from 0.01 to 1.5 kg. The temperature can be controlled to between 1 and 100° C., and include ranges such as 20 to 80° C., 15 to 95° C., 25 to 95° C., 45 to 90° C., 20 to 60° C., 50 to 80° C., or 25 to 75° C. Additionally, the flow rate of the recharging solution can be any one of 1 to 2,000 ml/min, 10 to 1,550 ml/min, 10 to 1,250 ml/min, 10 to 950 ml/min, 10 to 850 ml/min, 10 to 750 ml/min, 10 to 650 ml/min, or 10 to 550 ml/min. The conductivity of the recharging fluid can range from any one of 5 to 100 mS/cm, 20 to 80 mS/cm, 25 to 75 mS/cm, 35 to 65 mS/cm, 10 to 40 mS/cm, 45 to 55 mS/cm, or 55 to 100 mS/cm where mS/cm (Siemens equal 1/ohms). The recharging time can range from 1-60, 2-45, 5-40, 10-60, 1-10, 1-30, 25-60, 15-30, or 10-30 minutes. The volume of recharging fluid can range from any one of 0.65 to 32.5 L, 1.55 to 30.5 L, 2.50 to 25.5 L, 3.5 to 30.5 L, 5.0 to 27.5 L, 6.5 to 32.5 L, or 6.5 to 12.5 L. In one embodiment, a 0.5 M solution of NaOH was passed through a sorbent module containing 0.33 kg of zirconium oxide. The recharging solution can be controlled to be between 20 and 80° C. with a flow rate of 217 ml/min. The zirconium oxide can be recharged after about 30 minutes of the recharging process, necessitating about 6.5 L of recharging solution. In another embodiment, a 0.65 M solution of NaOH can be passed through a sorbent module containing 0.35 kg of zirconium oxide. The recharging solution can be controlled to be between 30 and 90° C. with a flow rate of 317 ml/min. The zirconium oxide can be recharged after about 25 minutes of the recharging process, necessitating about 7.5 L of recharging solution. In yet another embodiment, a 0.55 M solution of NaOH can be passed through a sorbent module containing 0.41 kg of zirconium oxide. The recharging solution can be controlled to be between 40 and 100° C. with a flow rate of 417 ml/min. The zirconium oxide can be recharged after about 15 minutes of the recharging process, necessitating about 6.0 L of recharging solution. One skilled in the art will understand that the variables listed can be changed and still recharge the zirconium oxide with a different amount of recharging solution, as necessary. In any embodiment of the first, second or third aspects of the invention, the recharger can be used for recharging zirconium phosphate or zirconium oxide. The recharger can comprise fluid sources containing recharging solutions for both zirconium oxide and zirconium phosphate, and the user may select which sorbent material to recharge. In any embodiment of the invention, the recharger can recharge multiple sorbent modules containing zirconium phosphate or multiple modules containing zirconium oxide.

In any embodiment of first, second or third aspects of the invention, when the zirconium oxide and the zirconium phosphate are recharged by the single recharger, the recharging conditions, including, but not limited to, the flow rate, temperature, conductivity, and duration can be controlled independently for each rechargeable material or module.

In any embodiment of first, second or third aspects of the invention, a zirconium phosphate recharging can include the steps of zirconium phosphate recharging 301, post-zirconium phosphate (post-ZP) rinsing 302, and draining 303, as shown in FIG. 4. The temperature of recharging can be maintained at between about 85° C. to 100° C. for a 30 minute recharging process. In any embodiment of the first, second or third aspects of the invention, the recharge solution can be maintained at between about 75° C. to 95° C. during the recharging process of step 301 for more than 10 to 30 minutes, for example 60 minutes.

In non-limiting examples, the pH of zirconium phosphate can be adjustable through titration during recharge. This can be important for zirconium phosphate if the pH required for proper recharge is different from the pH required for efficient cleaning. For example, a cleaning solution can be added either before or after the recharging step 301 to clean the zirconium phosphate. The cleaning solution can be any solution known in the art that can remove or deactivate undesired components on the zirconium phosphate. Further, a water rinsing step can occur after the cleaning step depending on the need for rinsing. The cleaning step can change the pH value of the zirconium phosphate, which can be titrated to a desired value by adding a separate acid feed to the recharger, or by using a different recharge solution that is controlled separately from the first recharge solution.

In any embodiment of the first, second or third aspects of the invention, a recharging process is not limited to a particular time of duration, and can be shortened or expanded based on a user's need or service sites, such as home, mobile stations, or dialysis centers. When the duration time is changed, other recharging conditions may also be changed, such as recharging temperatures.

At home dialysis refers to dialysis carried out by a user in his or her residence or other building outside of a clinical setting. At home dialysis may occur under hospice care or other medical supervision of doctors, nurses, or clinicians, but these are not always necessary. In order to facilitate recharging and reuse of sorbent materials in an at-home setting, the systems and methods are easily adaptable for use with the infrastructure common in homes having plumbing and electricity. However, at-home encompasses many other types of homes or out-of-clinic settings including homes and settings in less developed areas. The systems and methods can be used in those areas, countries, or locales where support infrastructure is minimal by relying on portable power generators and water reservoir tanks.

A mobile setting for dialysis refers to a movable dialysis setting. A mobile setting may comprise a mobile dialysis unit dispatched to one or more locations to provide dialysis to patients. The dialysis unit may be a large unit, capable of providing dialysis for multiple patients in a central location, or may be a smaller unit, capable of providing dialysis for only one or a few patients in a particular location. Often, a mobile dialysis unit may have little permanent infrastructure or support. The mobile dialysis unit may arrive at a location and set up a "pop-up" dialysis clinic, or a dialysis clinic that is only in a particular location for a brief time.

A dialysis center or clinic refers to a permanent location providing dialysis to patients. The dialysis center or dialysis clinic may employ doctors, nurses, or dialysis technicians to provide dialysis for multiple patients simultaneously. The dialysis clinics can be any size, ranging from clinics designed for one or two patients to clinics designed for dozens of patients or more.

A recharger system and method capable of working at a home, in a mobile setting or in a dialysis center provides for reuse of sorbent materials in these settings without the need to send the sorbent material to a recharging facility. Further, a recharger capable of operating without expensive and extensive infrastructure and support can facilitate use in these settings. As described, the recharger and method can be configured to allow easy use in non-traditional dialysis settings, facilitating home, mobile or clinic dialysis. In any embodiment of the first, second or third aspects of the invention, a user can use a sorbent cartridge in a dialysis session at one time of the day, and slowly recharge the sorbent cartridge or modules throughout the rest of the day, or portion of the day. For example, a user may undergo sorbent dialysis at night, and the sorbent modules can be recharged throughout the following day. This allows for a lower temperature recharging, and/or lower concentrations of recharging solutions, making the recharging solutions easier for users of varying skill. To facilitate the ability of mobile dialysis centers to provide treatment and then move on to a new location, a recharger as described requiring less infrastructure and that is easily used is important. In any embodiment of the first, second or third aspects of the invention, the recharging can be carried out in a dialysis center, or a clinic designed to carry out dialysis on multiple patients, under the control of doctors or technicians.

In non-limiting examples, the recharging time duration can have a broader range extending beyond 60 minutes. In a home or mobile environment, the recharging time duration may be traded off for lower system current drain. For example, the recharging can be performed for longer than 60 minutes, with lower temperature, which can lower heater demand to accommodate standard wall outlets that are more common in a home environment.

After the recharge solution passes through the zirconium phosphate, the rinsing step 302 can be performed using water. For example, a total volume of 3.00 L water can flow through the recharged zirconium phosphate at a rate of 600 ml/min for 5 minutes, under room temperature about 25° C. Rinse water may also be used to cool down the zirconium phosphate, if a high temperature solution is used for the recharge. Following the rinsing step 302, the zirconium phosphate can be drained by blowing air through the zirconium phosphate at step 303. For example, the air flow can be provided at 600 ml/min for 2 minutes at 25° C. In non-limiting examples, the zirconium phosphate can be contained in a module of a cartridge, where the steps 301-303 and related operations can be performed to the zirconium phosphate module, without removing the zirconium phosphate from the module.

The temperature of the water and flow rate can have any number of ranges. For example, the flow rate of the water can be any one of 25 and 1,500 ml/min, 100 and 1,250 ml/min, 375 and 875 ml/min, 400 and 750 ml/min, 250 and 650 ml/min, 300 and 700 ml/min, 200 and 800 ml/min, or 350 and 750 ml/min. Other ranges are contemplated by the invention and can be used without departing from the scope of the invention. The flow rate of the rinse water through the zirconium phosphate can be about 200, 300, 400, 500, 600, 700, 800, 900, or 1000 ml/min. The rinse time can range from 1-20, 2-18, 2-5, 2-6, 1-3, 2-3, 4-5, 4-6, or 3-6 minutes without departing from the scope of the invention. In specific embodiments, the flow rate can be 3.0 L of water at 600 ml/min at 25° C., for 5 minutes; 4.0 L of water at 550 ml/min at 28° C., for 8 minutes; 2.0 L of water at 750 ml/min at 29° C., for 4 minutes; or 4.5 L of water at 400 ml/min at 25° C., for 10 minutes.

The flow rate of the air blown through the zirconium phosphate or over the zirconium oxide can be between 100 and 1000 ml/min. In any embodiment, the flow rate of the air can be any one of 200 and 800 ml/min, 300 and 900 ml/min, 250 and 750 ml/min, 500 and 950 ml/min, 350 and 600 ml/min, 400 and 700 ml/min, 200 and 400 ml/min, or 300 and 800 ml/min. Other ranges are contemplated by the invention and can be used without departing from the scope of the invention. For example, in any embodiment of the first or second aspects of the invention, the flow rate of the air blown through the sorbent materials such as zirconium phosphate can be about 200, 300, 400, 500, 600, 700, 800, 900, or 1000 ml/min. When using a pump to draw air through the module by positive pressure, the pump can be capable of drawing air through the module at any rate, including between any of 200 and 800 ml/min, 300 and 900 ml/min, 250 and 750 ml/min, 500 and 950 ml/min, 350 and 600 ml/min, 400 and 700 ml/min, 200 and 400 ml/min, or 300 and 800 ml/min. The blowing time can range from 1-20, 2-18, 2-5, 2-6, 1-3, 2-3, 4-5, 4-6, or 3-6 minutes without departing from the scope of the invention. In specific embodiments, the flow rate can be 400 ml/min at 27° C., for 3 minutes; the flow rate can be 500 ml/min at 26° C., for 2 minutes; the flow rate can be 600 ml/min at 25° C., for 2 minutes; the flow rate can be 700 ml/min at 24° C., for 2 minutes; the flow rate can be 800 ml/min at 25° C., for 1 minutes; the flow rate can be 600 ml/min at 24° C., for 5 minutes; or the flow rate can be 600 ml/min at 23° C., for 7 minutes.

In any embodiment of the first or second aspects of the invention, the zirconium phosphate can be stored for any length of time, including between 1 min and 7 days, between 1 hour and 1 day, between 1 hour and 7 days, between 1 day and 7 days, between 1 day and 14 days, or between 7 days and 14 days. In any embodiment of the first or second aspects of the invention, the zirconium phosphate can be stored for any length of time, including more than 7 days.

In any embodiment of the invention, the zirconium phosphate can be contained within a reusable sorbent module. A sorbent cartridge for use in sorbent dialysis can include one or more reusable modules containing rechargeable materials and one or more single-use modules containing non-rechargeable or disposable materials. FIGS. 5a and 5b show non-limiting examples of the sorbent cartridges each having at least two reusable modules.

FIG. 5a shows that a sorbent cartridge can comprise a first reusable module 402 containing zirconium phosphate 405, a second reusable module 403 containing zirconium oxide 404, and a non-reusable module 401 containing different sorbent materials such as layers 406 and 408 of activated carbon and a layer 407 of urease and alumina. Activated carbon and urease and alumina can be replenished, or the sorbent module containing activated carbon and urease and alumina can be discarded after use.

In any embodiment of the first, second, and third aspects of the invention, FIG. 5a shows that a dialysate 400 can pass through the sorbent cartridge by first entering into the non-reusable module 401, then the first reusable module 402 and the second reusable module 403, before exiting the sorbent cartridge. Non-ionic toxins in the dialysate can be removed by activated carbon 408, urea can be broken down into ammonium ions and carbon dioxide by urease and alumina 407. Calcium, magnesium, potassium and ammonium ions in the dialysate can be removed by the zirconium phosphate 405, and any phosphate ions in the dialysate can be removed by the zirconium oxide 404. The second activated carbon layer 406 can serve to prevent urease migration out of the non-reusable module 401 and to remove any other non-ionic toxins still present in the dialysate.

In any embodiment of the first, second, or third aspects of the invention, the sorbent cartridge is not limited to the structure in FIG. 5a. For example, FIG. 5b shows that the sorbent cartridge can comprise of a first reusable module 410 containing zirconium phosphate 413, a second reusable module 411 containing zirconium oxide 412, and a third module 409 containing different sorbent materials such as layers 414 and 416 of activated carbon, a layer 407 of urease and alumina, and a layer of zirconium oxide 417. Zirconium oxide 417 and 412 can be provided upstream and downstream of zirconium phosphate 413. A dialysate 418 can pass through sequentially the third module 409, the first reusable module 410 and the second reusable module 411 of the sorbent cartridge, to remove the non-toxins, and cations, and phosphate ions in the dialysate. However, the dialysate may not necessarily pass the sorbent cartridge in the above described order, and may possibly bypass one or more layers or modules in the sorbent cartridge.

In any embodiment of the first, second, or third aspects of the invention, the reusable modules, for example, the first reusable module 402 of FIG. 5a, can be detached from the sorbent cartridge, and subsequently be connected to a recharger for recharging. The rechargeable material zirconium phosphate 405 may not need to be removed from the corresponding module, and instead, can be recharged while remaining within the modules 402 or 413. Zirconium oxide 404 can also be recharged without being removed from the second reusable module 403. Recharging zirconium phosphate and zirconium oxide contained in the modules of the sorbent cartridge can provide significant convenience to a user, and also improve the efficiency of an overall recharging process. One skilled in the art will understand that anion exchange resins can be used in place of the zirconium oxide, such as strong acid or weak acid anion exchange resins.

Figure 6:
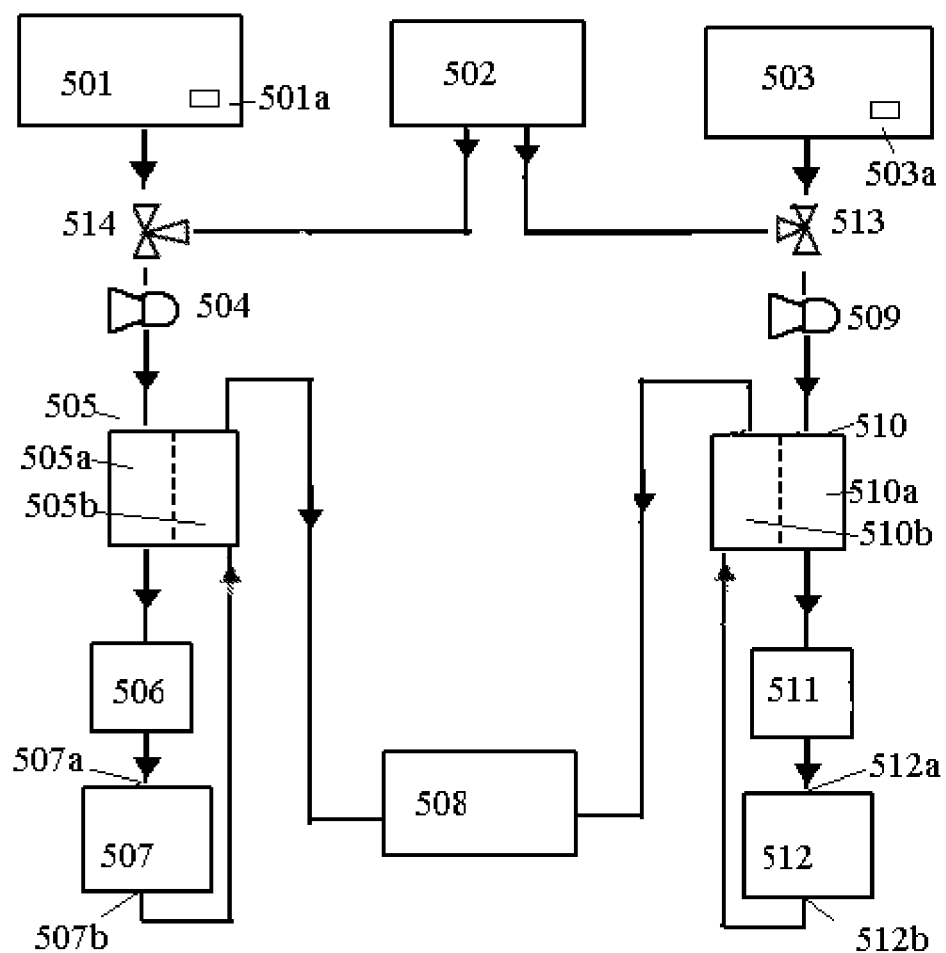
FIG. 6 shows a flow path for recharging two different rechargeable materials, such as zirconium phosphate and zirconium oxide.

FIG. 6 shows a flow diagram for a recharger that is configured to recharge both a zirconium phosphate containing module 507 and a zirconium oxide containing module 512. A first fluid source, such as recharging solution tank 501 can contain a zirconium phosphate recharging solution, such as a sodium/buffer solution, and a second fluid source, such as recharging solution tank 503 can contain a zirconium oxide recharging solution, such as NaOH solution. In FIG. 6, the zirconium phosphate recharging solution can exit from the tank 501 via a valve 514 to enter into the zirconium phosphate module 507 through an inlet 507a by passing through a first compartment 505a of a heat exchanger 505 and heater 506. After exiting from the zirconium phosphate module 507 via an outlet 507b, the used recharging solution can pass back through heat exchanger 505 in a second compartment 505b. This will heat up the fresh zirconium phosphate recharging solution in the first compartment 510a of heat exchanger 510, reducing the requirements for heater 511 to heat the solution to a desired temperature. After passing through heat exchanger 505, the used zirconium phosphate recharging solution can be directed to a drain or storage container 508. Water source 502 can be used to rinse the zirconium phosphate module 512 after recharging, by switching valve 514 or to rinse the fluid lines of the recharger prior to recharging the zirconium phosphate and zirconium oxide or after recharging the zirconium phosphate and zirconium oxide. Pump 504 can provide the driving force for the zirconium phosphate recharge solution or water to move through the zirconium phosphate side of the recharger.

FIG. 6 also shows a fluid source containing a zirconium oxide recharging solution can be zirconium oxide recharging solution tank 503. The zirconium oxide recharging solution can pass through valve 513, a first compartment 510a of a heat exchanger 510 and heater 511 before entering into zirconium oxide module 512 via an inlet 512a. The used zirconium oxide recharging solution can then exit from zirconium oxide module 512 via an outlet 512b, and pass through a second compartment 510b of the heat exchanger 510, heating up the solution in the first compartment 510a and reducing the requirements for heater 511 to heat the solution to a desired temperature. After passing through heat exchanger 510, the used zirconium oxide recharging solution can be directed to a drain or storage container 508. Pump 509 can provide the driving force necessary to move fluid through the zirconium oxide side of the recharger.

In any embodiment of the first, second, or third aspects of the invention, one or more sensors can be provided to monitor pH/conductivity or any other characteristics of the recharging solution to ensure the correct composition. For example, the zirconium phosphate recharging solution can be monitored by a sensor 501a located within the tank 501, and the zirconium oxide recharging solution can be monitored by a sensor 503a located within the tank 503. A person skilled in the art will understand that the sensors can be provided at any other places along the flow paths of the recharging solutions.

The zirconium oxide module 512 can be rinsed with water from water source 502 through switching valve 513. One skilled in the art will understand that separate water sources for the zirconium phosphate and zirconium oxide modules are possible, but not necessary. Further, separate drains or storage containers are also possible but not necessary.

In any embodiment of the first, second, or third aspects of the invention, the storage container 508 can comprise a mixer, so that the recharging fluids can be continuously neutralized for disposal. Because the zirconium phosphate recharging fluid can be acidic or contain sodium/buffer solution with an acidic pH value, while the zirconium oxide recharging fluid is basic, combining the used fluids in a single container 405 with a mixer will cause the used recharging fluids to be neutralized and easily disposed. Zirconium phosphate module 507 and zirconium oxide module 512 can be recharged with the same recharger or with different rechargers. The recharging solution tanks 501 and 503 can be fluidly connected to their corresponding heat exchangers 505 and 510, heaters 506 and 511, and modules 507 and 512, respectively, in any form known to the art.

In any embodiment of the first, second or third aspect of the invention, a recharger flow loop for recharging both zirconium phosphate and zirconium oxide is not limited to the steps and structures shown in FIG. 6. For example, a single heat exchanger can be used for both the zirconium phosphate and zirconium oxide recharging solutions by separating the single heat exchanger into additional compartments (not shown) for the fresh and used recharging solutions to pass through. A single heater containing multiple compartments can also be used to heat up different recharging solutions (not shown). When a single heater or a single heat exchanger is used, the desired temperature for recharging the zirconium oxide and zirconium phosphate can be adjusted for consistency. However, different temperatures can be desired for each of the zirconium phosphate recharging solution and the zirconium oxide recharging solution, even with the recharging system using a single heater and heat exchanger. For example, the flow rates of each of the solutions can be controlled independently, so that allowing differing conditions such as temperatures for each of the zirconium phosphate and zirconium oxide modules may have conditions, such as temperatures, different from each other.

In any embodiment of the first, second, third aspects of the invention, modification of a component shown in FIG. 6 of the recharging system, such as using the single heat exchanger or the single heater, can result in additional changes in structures or operation steps in the recharging system, in order to achieve the desired recharging outcome.

Figure 7:
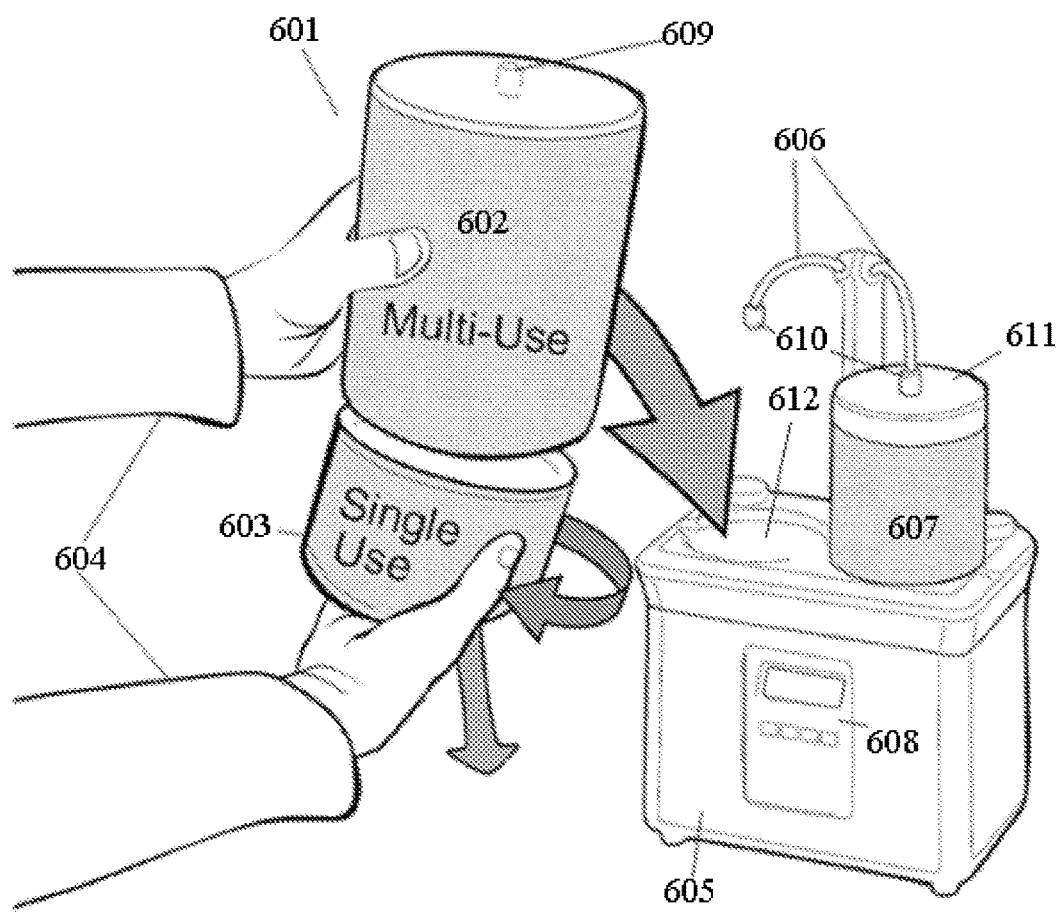
FIG. 7 shows a recharger configured to recharge one or more sorbent modules.

FIG. 7 shows a process of recharging a sorbent module of the first, second, and third aspects of the invention, having a rechargeable sorbent material, specifically, zirconium phosphate. The sorbent cartridge 601 of FIG. 7 can be a modular dialysate regeneration assembly. As explained, a modular dialysate regeneration assembly can be one or more sorbent compartments or sorbent modules containing at least one sorbent material attached to at least another sorbent compartment or sorbent module. That is, the sorbent cartridge 601 can comprise multiple modules. Each module can be detachably connected to the other module or modules. The modules, when attached can form a fluid connection as described herein, when the fluid flows from one module into another. The modules can be detached as shown in FIG. 7 into separate components to facilitate the recharging of rechargeable sorbent materials. The sorbent cartridge 601 may contain a multi-use module 602 which contains zirconium phosphate, and a single-use module 603 which comprises other sorbent materials, such as activated carbon, alumina, silica, urease, hydrous zirconium oxide and ion-exchange resin. Single use module 603 can also contain zirconium phosphate that is not intended to be recharged. In any embodiment of the first, second, and third aspects of the invention, the sorbent cartridge 601 can be a single structure, with all sorbent materials in the same module. After use, the functional capacity of the modules may be reduced due to the binding of solutes from spent dialysate to the sorbent materials within the sorbent cartridge. The user 604 can disconnect the single-use module 603 from the multi-use module 602. The single use module can be discarded or sent to a recharging or replenishing facility for recharging or replenishing. The multi-use module 602 can be recharged in order to restore the functional capacity of the sorbent materials as described herein. The multi-use module 602 can also be replenished to add back sorbent materials into the multi-use module 602.

One skilled in the art will understand that the sorbent cartridge 601 can comprise more than two modules, including sorbent cartridges with three, four, five or more modules. For example, a bank of modules containing any combination of zirconium phosphate and/or zirconium oxide modules can be recharged with fluid connections, tanks, and appropriate fluid lines constructed for such multiple charging. The number of modules being charged at any one time can include a range from 3 to 6, 4 to 8, 5 to 10, 6 to 12, 7 to 14 or more. The total number of modules in the bank can be any number 2 or greater. For example, a bank may contain, 3, 4, 5, 6, 7, 8, 9, 10, 11, 12, 13, or more multi-use modules. In any embodiment of the first or second aspects of the invention, the recharger can set the flow rates, temperatures and concentrations of the recharging solutions independently for each module or group of modules. A recharger that can accommodate a single multi-use module may be a preferred recharger for use in a home or other environments. Multiple module rechargers may be preferred in different environments. Additional modules may be multi-use, such as modules containing zirconium oxide which can be recharged as explained.

FIG. 7 shows that the recharging apparatus such as the recharger 605 can comprise a sorbent cartridge fluid inlet 606 and a sorbent cartridge fluid outlet (not shown), as shown by recharging sorbent module 607. The fluid inlet 606 can connect to the modules by attaching recharger connector 610 to sorbent module connector 609 (only shown for module 602). The proper solutions as described herein can pass through the multi-use or reusable modules as needed, such as with multi-use module 607 located on the recharger 605. Interface 608 can be used to notify the user of the progress of the recharging process, or can be used by the user to select the proper solutions, concentrations, amounts, temperature or other variables described herein for the recharging process. In any embodiment of the first, second, and third aspects of the invention, instead of the recharge connector 610 attaching directly to connector 609 on the multi-use module 602, a separate connector 611 can be fitted to the multi-use module, as is shown with multi-use module 607. This connector 611 can fit over the top of the multi-use module 607 and facilitate the introduction of recharging solution into the multi-use module 607.

In non-limiting examples, the recharger 605 can be configured to recharge a single multi-use module 607 as this may be a preferred configuration for the home environment. The recharger 605 configured to recharge a single multi-use module 607 may also be used in a dialysis center or a mobile station. The single multi-use module 607 can contain one rechargeable material, such as zirconium phosphate or zirconium oxide. The single multi-use module 607 may also contain mixed rechargeable materials such as a mixture of zirconium phosphate and zirconium oxide. The recharger 605 can be configured to recharge multiple multi-use modules, such as a zirconium phosphate cartridge and a zirconium oxide cartridge.

A recharger can also have configurations that are specifically designed to fit into different sites of service, such has home, mobile, dedicated sorbent based dialysis clinics, in the first, second, and third aspects of the present invention. Rechargers that have the ability to recharge multiple multi-use modules and can accommodate different service sites are contemplated by this invention.

In any embodiment of the first, second, and third aspects of the invention, the recharger 605 can accommodate multiple multi-use sorbent modules at the same time, such as both multi use sorbent modules 602 and 607 in FIG. 7. Multi-use sorbent module 602 can be placed in space 612 while the recharger 605 is recharging multi use module 607. One skilled in the art will understand that the invention is not limited to recharging systems that can accommodate two multi-use modules at the same time. Systems that can only accommodate a single multi-use module, as well as systems that can accommodate 3, 4, 5, or more multi-use modules simultaneously are contemplated by this invention.

Examples of Recharge Solutions

In a non-limiting example, a custom synthesized zirconium phosphate 20.9 grams, was loaded into a 1" ID jacketed column. For the first step, the zirconium phosphate was treated with a recharge solution of NaCl, NaAce and HAce. The recharge solution, 90-ml, was passed through the zirconium phosphate at a flow rate of 8 ml/min at a temperature of 80° C. The column was then rinsed with 50 ml of deionized water at a flow rate of 5 ml/min and a column temperature of 37° C. Then a breakthrough (BT) run was performed using a solution of 105 mM sodium chloride, 25 mM sodium bicarbonate, 20-mM ammonium chloride, 3 mM potassium chloride, 1.5 mM calcium chloride and 0.5-mM magnesium chloride at a pH of 7.5, which is fed through the column at 10 ml/min for 120 minutes at a temperature of 37° C. The pH exiting the column (effluent pH) was measured using an in-line pH sensor [Mettler-Toledo]. After the breakthrough run the column was rinsed with 300 ml deionized water at 10 ml/min at 37° C. After the breakthrough run and rinse the recharge method described above was repeated, along with the first rinse step described above. Then, another breakthrough run was performed and the effluent pH was again recorded.

Figure 8:
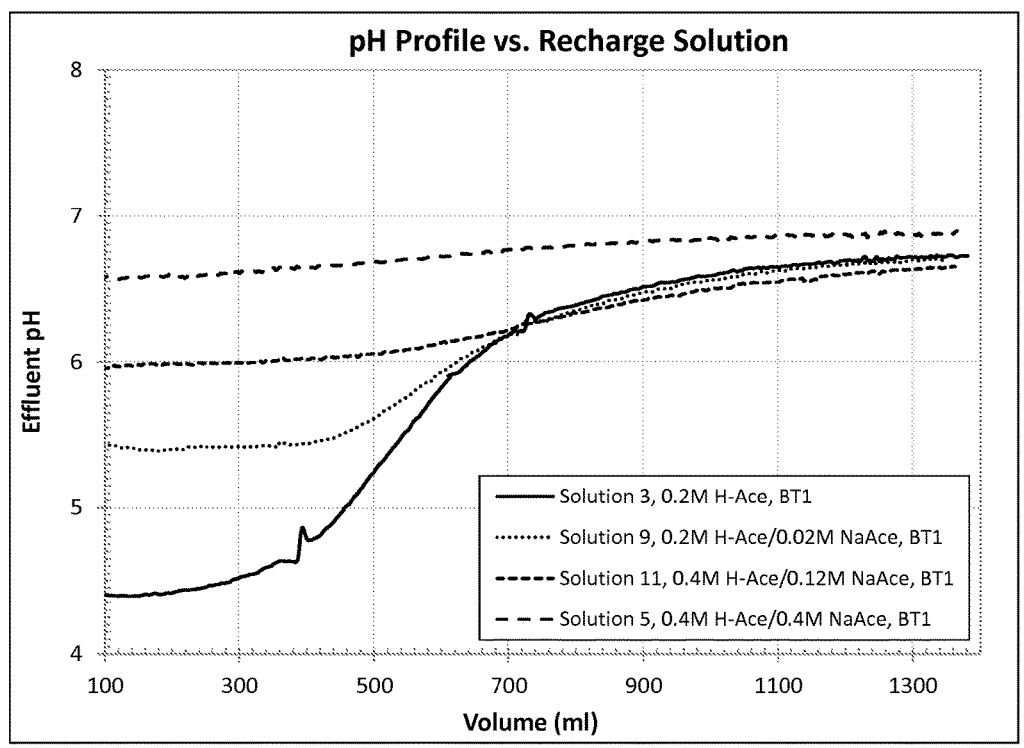
FIG. 8 shows pH profiles for different recharge solutions passing through a rechargeable material, such as zirconium phosphate.
Figure 9:
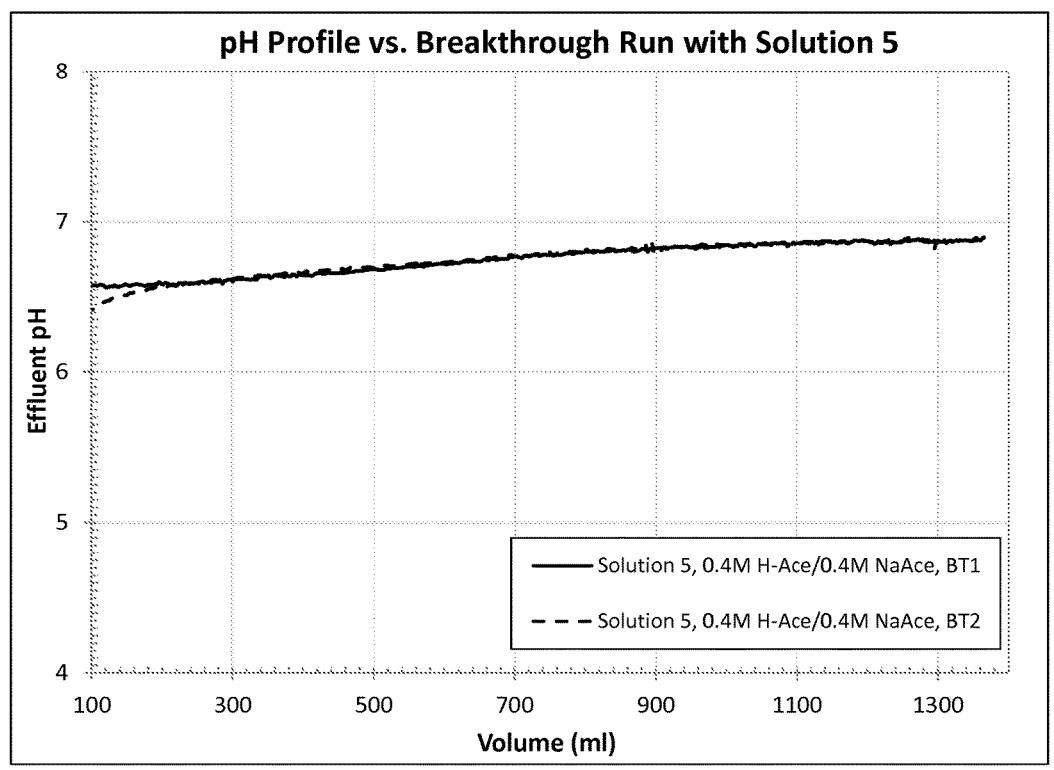
FIG. 9 shows pH profiles for two breakthrough runs of a zirconium phosphate recharge solution.
Figure 10:
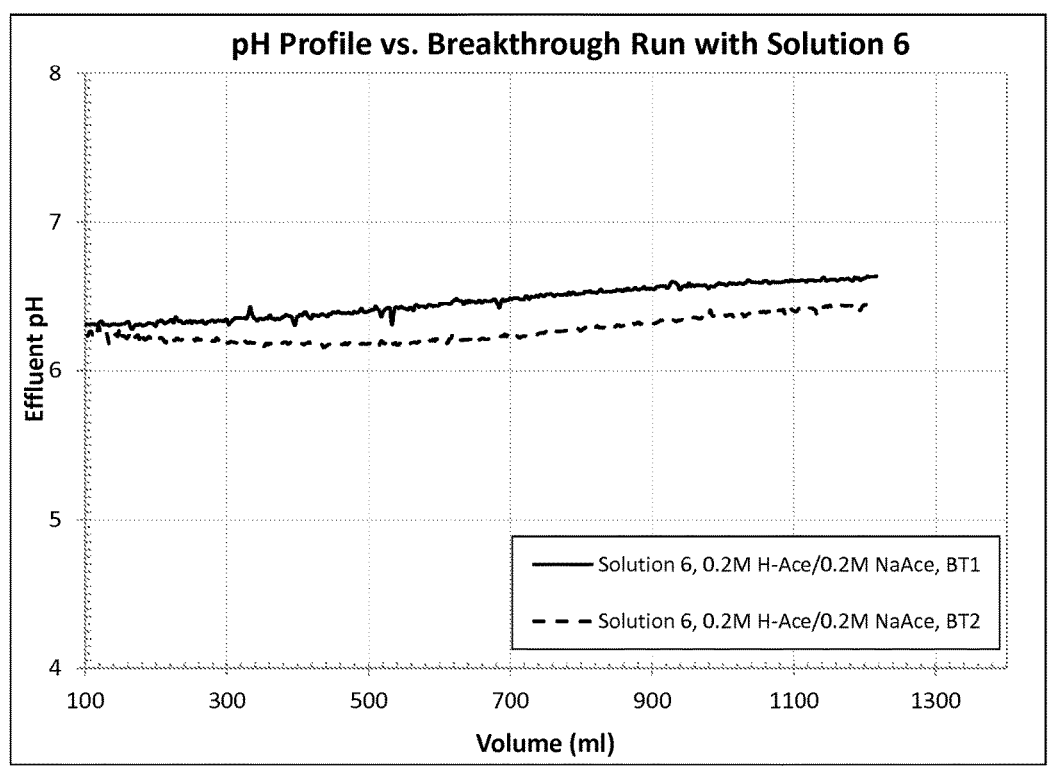
FIG. 10 shows pH profiles for two breakthrough runs of a zirconium phosphate recharge solution.

Substantially consistent pH profiles are desired during the zirconium phosphate breakthrough runs regardless of how much ammonium, potassium, calcium and magnesium have been loaded onto the zirconium phosphate before recharging. FIGS. 8 through 10 show effects on the effluent pH for various recharge solutions passing through spent zirconium phosphate in non-limiting examples. FIG. 8 shows effluent pH profiles during a breakthrough run for recharge solutions containing different concentrations of sodium/buffer, for example, solutions 3, 5, 9, and 11 listed in Table 1. In FIG. 8, a zirconium phosphate sample recharged with solution 5 displays the most consistent effluent pH during breakthrough for the zirconium phosphate. A zirconium phosphate sample recharged with solution 3 displays the least consistent effluent pH profile. That is, solution 5 results in zirconium phosphate that maintains a substantially consistent pH throughout the breakthrough run, while solution 3 results in zirconium phosphate that does not maintain a substantially consistent pH during the breakthrough run.

In FIG. 8, recharging zirconium phosphate with solution 5 results zirconium phosphate that maintains a substantially consistent pH throughout the breakthrough runs, as the pH of the effluent during the breakthrough run is consistently maintained between about 6.6 and 6.9. Similarly, recharging zirconium phosphate with solution 11 results in zirconium phosphate that maintains a substantially consistent pH throughout the breakthrough runs, as the pH of the effluent during the breakthrough run is maintained between about 5.9 and 6.6. In contrast, recharging zirconium phosphate with solution 3 does not result in zirconium phosphate that maintains a substantially consistent pH throughout the breakthrough run, as the pH of the effluent during the breakthrough run varies from about 4.5 to about 6.6.

In any embodiment of the first, second, or third aspects of the invention, the total acetate, or buffer capacity of the recharge solution can be critical to achieve similar pH profiles during BT1 and BT2. Breakthrough 1 (BT1) shows the pH profile after recharging a zirconium phosphate that has not been loaded with any cations and breakthrough 2 (BT2) shows the pH profile after recharging a zirconium phosphate that has been loaded with 24 mmols ammonium, 3.6 mmols potassium, 1.8 mmols calcium and 0.6 mmols magnesium. FIGS. 9 and 10 show differences between BT1 and BT2 pH profiles using recharge solutions 5 and 6 in Table 1, respectively. Solution 6 contains 0.2M HAce and 0.2M NaAce, and solution 5 contains 0.4M HAce and 0.4M NaAce. The higher acetate concentration, and resulting higher buffer capacity, in solution 5 results in more consistent pH profiles during BT1 and BT2.

One skilled in the art will understand that various combinations and/or modifications and variations can be made in the described systems and methods depending upon the specific needs for operation. Moreover features illustrated or described as being part of an aspect of the invention may be used in the aspect of the invention, either alone or in combination.

We claim:

1. A solution for recharging zirconium phosphate, comprising a combination of at least one sodium salt and at least one acid, the solution having a predetermined pH value that results in a substantially consistent pH in a dialysate passing through the zirconium phosphate after the solution is used for recharging zirconium phosphate.

2. The solution of claim 1, wherein the solution is selected from the group consisting of sodium acetate /acetic acid solution, glycolic/glycolate solution, citric/citrate solution, propionate/propionic solution, phosphate-monobasic solution, or any combination thereof.

3. The solution of claim 1, wherein the solution consists essentially of sodium chloride, sodium acetate and acetic acid.

4. The solution of claim 3, wherein concentrations of the sodium chloride, the sodium acetate, and the acetic acid are about 3.60M, 0.40M, and 0.40M, respectively, or about 3.88M, 0.12M, and 0.40M, respectively.

5. The solution of claim 3, wherein a concentration of acetic acid in the solution is greater than or equal to a concentration of sodium acetate in the solution.

6. The solution of claim 1, wherein the solution is a buffer solution.

7. The solution of claim 6, wherein the buffer solution has a pH of between any of about 4 and about 8, about 4.5 and about 6, about 6 and about 7, or about 5.5 and about 7.5.

8. The solution of claim 1, wherein the solution consists essentially of sodium chloride and sodium monobasic phosphate.

9. The solution of claim 8, wherein concentration of the sodium chloride is between about 3.20 M and about 4.0 M and wherein the concentration of the sodium monobasic phosphate is between about 0.05 M and about 0.8 M.

10. The solution of claim 8, wherein the pH of the solution is between any of about 2 and about 8, about 3 and about 5, about 3.5 and about 4.8, or about 4.0 and about 4.5.

11. The solution of claim 1, wherein the solution comprises glycolic acid.

12. The solution of claim 1, wherein the solution has a pH that results in a pH of between 5.9 and 6.9 in the dialysate passing through the zirconium phosphate after the solution is used for recharging zirconium phosphate.

13. The solution of claim 1, wherein the solution contains glycolic acid and sodium glycolate.

14. The solution of claim 1, wherein the solution contains citric acid and sodium citrate.

15. The solution of claim 1, wherein the solution contains propionic acid and sodium propionate.

16. A method of recharging zirconium phosphate in a rechargeable sorbent module, comprising the step of passing the solution of claim 1 through the rechargeable sorbent module.

17. The method of claim 16, wherein the solution is generated by mixing at least two different solutions in a recharger.

18. The method of claim 17, wherein the solution is generated by mixing an acetic acid solution, a sodium acetate solution, and a sodium chloride solution.

19. The method of claim 17, wherein the solution is generated by mixing an acetic acid solution, and a solution containing sodium acetate and sodium chloride.

20. The method of claim 16, further comprising the step of heating the solution prior to passing the solution through the rechargeable sorbent module.

\* \* \* \* \*